(12) United States Patent
Anderson et al.

(10) Patent No.: US 7,163,808 B2
(45) Date of Patent: Jan. 16, 2007

(54) ARTERY SMOOTH MUSCLE- AND VEIN SMOOTH MUSCLE-SPECIFIC PROTEINS AND USES THEREFOR

(75) Inventors: David J. Anderson, Altadena, CA (US); Guillermo Garcia-Cardena, Boston, MA (US); Michael A. Gimbrone, Jr., Plain, MA (US); Hai U. Wang, Eldorado Hills, CA (US)

(73) Assignees: California Institute of Technology, Pasadena, CA (US); The Brigham and Women's Hospital, Inc., Boston, MA (US)

( * ) Notice: Subject to any disclaimer, the term of this patent is extended or adjusted under 35 U.S.C. 154(b) by 608 days.

(21) Appl. No.: 09/988,496

(22) Filed: Nov. 20, 2001

(65) Prior Publication Data

US 2002/0136726 A1   Sep. 26, 2002

Related U.S. Application Data

(60) Provisional application No. 60/252,009, filed on Nov. 20, 2000.

(51) Int. Cl.
| | |
|---|---|
| C12P 21/04 | (2006.01) |
| C12N 5/00 | (2006.01) |
| C12N 15/00 | (2006.01) |
| A01K 67/00 | (2006.01) |

(52) U.S. Cl. ............... 435/70.1; 435/325; 435/455; 800/8

(58) Field of Classification Search ............. 435/325, 435/6
See application file for complete search history.

(56) References Cited

U.S. PATENT DOCUMENTS

| | | | | |
|---|---|---|---|---|
| 6,015,711 | A * | 1/2000 | Olson et al. | 435/375 |
| 6,440,954 | B1 * | 8/2002 | Haber et al. | 514/169 |
| 6,864,227 | B1 * | 3/2005 | Wang et al. | 514/2 |
| 6,887,674 | B1 * | 5/2005 | Wang et al. | 435/7.21 |
| 6,916,625 | B1 * | 7/2005 | Wang et al. | 435/7.21 |

FOREIGN PATENT DOCUMENTS

| | | |
|---|---|---|
| EP | 0 633 315 A2 | 1/1995 |
| EP | 0 999 278 A1 | 5/2000 |
| WO | WO 96/26958 | 2/1996 |
| WO | WO 99/52541 | 10/1999 |
| WO | WO 00/30673 | 6/2000 |

OTHER PUBLICATIONS

Yamamoto et al. Stroke 29:1188-1193, 1998.*

Bennett, B. D., et al., "Molecular Cloning of a Ligand for the EPH-Related Receptor Protein-Tyrosine Kinase Htk," *Proc. Natl. Acad. Sci. USA*, 92:1866-1870 (1995).

Bergemann, A. D., et al., "ELF-2, a New Member of the Eph Ligand Family, Is Segmentally Expressed in Mouse Embryos in the Region of the Hindbrain and Newly Forming Somites," *Mol. Cell. Biol.*, 15(9):4921-4929 (1995).

Stein, E., et al., "Eph Receptors Discriminate Specific Ligand Oligomers to Determine Alternative Signaling Complexes, Attachment, and Assembly Responses," *Genes Dev.* 12:667-678 (1998).

Andres, A.-C., et al., "Expression of Two Novel Eph-Related Receptor Protein Tyrosine Kinases in Mammary Gland Development and Carcinogenesis," *Oncogene*, 9:1461-1467 (1994).

Folkman, J., et al., "Blood Vessel Formation: What Is Its Molecular Basis?" *Cell*, 87:1153-1155 (1996).

Risau, W., Mechanisms of Angiogenesis, *Nature*, 386:671-674 (1997).

Pasquale, E. B., "The Eph Family of Receptors," *Curr. Opin. Cell. Biol.* 9:608-615 (1997).

Wang, H. U., et al., "Eph Family Transmembrane Ligands Can Mediate Repulsive Guidance of Trunk Neural Crest Migration and Motor Axon Outgrowth," *Neuron*, 18:383-396 (1997).

Asahara, T., et al., "Isolation of Putative Progenitor Endothelial Cells for Angiogenesis," *Science*, 275:964-967 (1997).

Fabes et al., "Accumulation of the Inhibitory Receptor EphA4 May Prevent Regeneration of Corticospinal Tract Axons Following Lesion," *Eur. J. Neurosci.*, 23(7):1721-1730 (2006) (Abstract).

* cited by examiner

*Primary Examiner*—Joseph Woitach
(74) *Attorney, Agent, or Firm*—Fish & Neave IP Group Ropes & Gray LLP

(57) ABSTRACT

Arterial and venous smooth muscle cells are molecularly distinct from the earliest stages of angiogenesis through to adulthood. This distinction is revealed by expression on arterial cells (e.g., arterial endothelial cells, arterial smooth muscle cells) of a transmembrane ligand, called EphrinB2 whose receptor EphB4 is expressed on venous cells. Targeted disruption of the EphrinB2 gene prevents the remodeling of veins from a capillary plexus into properly branched structures. Moreover, it also disrupts the remodeling of arteries, suggesting that reciprocal interactions between pre-specified arterial and venous cells are necessary for angiogenesis. Expression of EphrinB2 in arterial cells (e.g., arterial endothelial cells, arterial smooth muscle cells) can be used to advantage in methods for targeting agents and/or encoded polypeptides to arterial smooth muscle cells, altering angiogenesis, assessing the effect of agents on arterial smooth muscle cells, identifying arterial smooth muscle cells, isolating arterial smooth muscle cells and production of artificial vessels, for example.

8 Claims, 2 Drawing Sheets

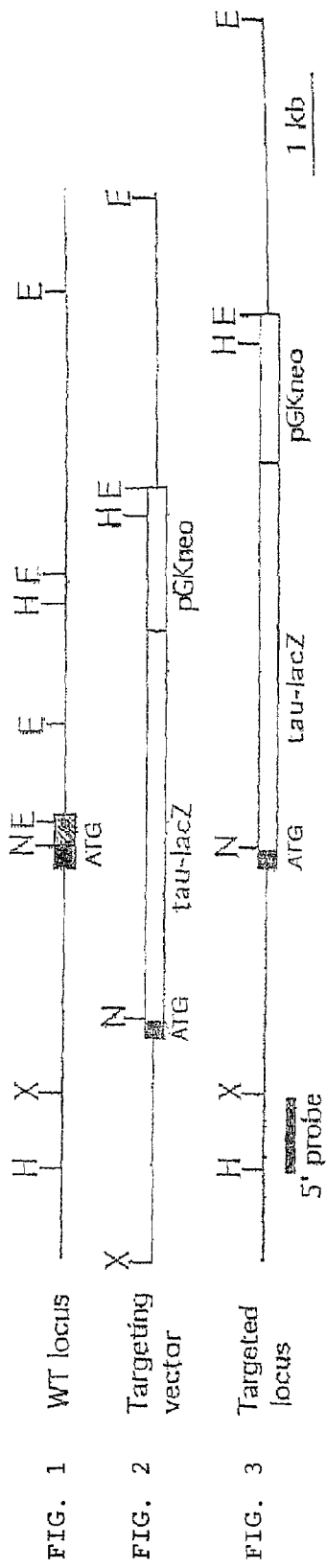

ARTERY SMOOTH MUSCLE- AND VEIN SMOOTH MUSCLE-SPECIFIC PROTEINS AND USES THEREFOR

RELATED APPLICATIONS

This application claims the benefit of U.S. Provisional Application No. 60/252,009, filed Nov. 20, 2000, the entire teachings of which are incorporated herein by reference.

GOVERNMENT SUPPORT

The invention was supported by grant R37-HL51150 from the American Heart Association and grant P50-HL56985 from the National Heart, Lung and Blood Institute. The Government has certain rights in the invention.

BACKGROUND OF THE INVENTION

The process of blood vessel formation is fundamental in both development and disease. The circulatory system is the first organ system to emerge during embryogenesis, and is necessary to nourish the developing fetus. Disorders of the circulatory system, such as coronary artery disease, are a major cause of morbidity and mortality in modern society. Thus, repairing, replacing and promoting the growth of blood vessels is a major target of clinical research and of pharmaceutical development. Conversely, the ingrowth of new capillary networks into developing tumors is essential for the progression of cancer. Thus, the development of drugs that inhibit this process of tumor angiogenesis is an equally important therapeutic goal. Little attention has been paid to the problem of how arteries and veins acquire their distinct identities. Indeed, many people have assumed that the anatomical and functional differences between arteries and veins simply reflect physiological influences, such as blood pressure, oxygenation and shear forces. Additional knowledge of how arteries and veins acquire their respective identities would be valuable in both research and clinical settings.

SUMMARY OF THE INVENTION

The present invention relates to a method of distinguishing between arterial cells (including arterial smooth muscle cells) and venous cells (including venous smooth muscle cells) based preferentially on the expression of a protein on arterial cells (e.g., arterial endothelial cells, arterial smooth muscle cells) and not (or to a lesser extent) on venous cells. The invention also relates to a wide variety of processes, methods and compositions of matter, including those useful in research and clinical settings, which are based on the difference in expression between arterial cells and venous cells. As described herein, it has been shown that there is a molecular distinction between arterial cells (e.g., arterial endothelial cells, arterial smooth muscle cells) and venous cells (e.g., venous endothelial cells, venous smooth muscle cells). Thus, arterial cells (e.g., arterial endothelial cells, arterial smooth muscle cells) and venous cells (e.g., venous endothelial cells, venous smooth muscle cells) bear molecular markers which can be used to identify, separate, target, manipulate or otherwise process each cell type specifically (separate from the other). As a result, arteries and veins can now be distinguished from one another, and cell types that make up arteries and veins can be assessed for other genetic, molecular and/or functional differences. This allows arteries and arterial cells (e.g., arterial endothelial cells, arterial smooth muscle cells), as well as veins and venous cells (e.g., venous endothelial cells, venous smooth muscle cells), to be targeted, manipulated or otherwise processed individually or separately for research, diagnostic and/or therapeutic purposes.

The present invention relates to methods of distinguishing and separating arterial cells from venous cells, and more specifically, distinguishing and separating arterial smooth muscle cells from venous smooth muscle cells based on their respective molecular markers; methods of selectively targeting or delivering agents, drugs, nucleic acids and/or gene products to arteries (and in particular to arterial smooth muscle cells) or veins; methods of altering (enhancing or inhibiting, where "inhibiting" includes partially or completely inhibiting) the function of artery-specific or vein-specific molecular markers or interaction between them (and, thus, enhancing or inhibiting the effect such functions or interactions have on arterial smooth muscle cells or venous smooth muscle cells); and methods of screening for drugs which act selectively on arterial cells (and more specifically, on arterial smooth muscle cells) or venous cells (and more specifically, on venous smooth muscle cells).

As used herein, "selectively" and "specific" include differential expression of arterial and vein proteins. As used herein, "not expressed" includes differential expression which is capable of being measured by techniques known to those skilled in the art.

The invention also relates to transgenic nonhuman mammals, such as transgenic mice, in which genes encoding an arterial cell molecular marker (e.g., an arterial smooth muscle marker) or a venous cell molecular marker (e.g., a venous smooth muscle marker) are altered, either physically or functionally, and their use as "indicator mice" to specifically visualize either arteries and arterial cells (e.g., arterial endothelial cells, arterial smooth muscle cells) or veins, to isolate such arterial (or venous) cells, to assess the function of the molecular marker which has been altered and to identify drugs which affect (enhance or inhibit) their function. It further relates to antibodies which bind an arterial cell-specific marker (e.g., an arterial smooth muscle marker) or a venous cell-specific marker (e.g., a venous smooth muscle marker); viral or other vectors targeted to arteries (e.g., arterial smooth muscle cells) or veins (e.g., venous smooth muscle cells) by virtue of their containing and expressing, respectively, an arterial cell-specific marker (e.g., an arterial smooth muscle marker) or a venous cell-specific marker (e.g., a venous smooth muscle marker); cDNAs useful for preparing libraries to be screened for additional artery- or vein-specific genes, and in particular arterial smooth muscle cell-specific genes and venous smooth muscle cell-specific genes, and immortalized cell lines derived from isolated arterial cells (e.g., arterial smooth muscle cells), from venous cells (e.g., venous smooth muscle cells), or from transgenic animals (e.g., mammals, such as mice, rats, guinea pigs, pigs or sheep) of the present invention.

A molecular marker for an arterial cell or a venous cell is any gene product (protein or RNA or combination thereof) expressed by one of these cell types and not by the other. Such a marker can be an artery-specific (e.g., arterial smooth muscle cell-specific) or vein-specific (e.g., venous smooth muscle cell-specific) product or protein. In specific embodiments, these can be referred to, respectively, as arterial smooth muscle cell-specific (artery-specific) ligands and venous smooth muscle cell-specific (vein-specific receptors). Such molecular markers can be expressed on cell types in addition to arterial or venous cells, but are not expressed (or are not expressed to the same extent) on both arterial and venous cells. Molecular markers can include, for example, mRNAs, proteins, members of ligand-receptor pairs (e.g., Ephrin family ligands and Eph family receptors), or any other proteins (e.g., adhesion proteins, transcription factors, antigens) which are not expressed equivalently on both cell types. In one embodiment, the molecular marker is a membrane receptor which is a receptor for a growth factor which acts on arteries or veins. In another embodiment the molecular marker is a member of a smooth muscle cell surface ligand-receptor pair which is differentially expressed on arterial and venous smooth muscle cells. For example, as described in detail herein, a member of the Ephrin family of ligands is a molecular marker for arterial smooth muscle cells and can be used to distinguish or isolate arterial smooth muscle cells. Any Ephrin family ligand or Eph family receptor which is preferentially expressed on arterial smooth muscle cells, but is not expressed (or is expressed to a measurably lesser extent) on venous smooth muscle cells, can be used to distinguish between arteries and veins. Similarly, any Ephrin family ligand or Eph family receptor which is preferentially expressed on venous smooth muscle cells, but not at all (or to a measurably lesser extent) on arterial smooth muscle cells, can be used to distinguish between arteries and veins.

In certain embodiments, the present invention relates to the discovery that arterial smooth muscle cells express an Ephrin family ligand; methods of distinguishing or separating arterial cells (arteries) from venous cells (veins), e.g., separating arterial smooth muscle cells from venous smooth muscle cells; methods of selectively targeting or delivering drugs or agents to arteries (e.g., arterial endothelial cells, arterial smooth muscle cells) or veins (e.g., venous endothelial cells, venous smooth muscle cells); methods of enhancing (promoting) or inhibiting angiogenesis, including angiogenesis in tumors, such as by altering (increasing, decreasing or prolonging) activity of at least one member of an Ephrin family ligand-cognate Eph family receptor pair and drugs useful in the methods; and methods of screening for drugs which preferentially act on arteries or veins.

It further relates to transgenic animals (e.g., mammals, such as transgenic mice, rats, guinea pigs, pigs or sheep) which have altered genes encoding an Ephrin family ligand (e.g., EphrinB2 knockout mice which contain a tau-lacZ (tlacZ) insertion that marks arteries but not veins), or altered genes encoding an Eph family receptor (e.g., EphB4 knockout mice which contain a reporter construct (e.g., lacZ or alkaline phosphatase gene) in the EphB4 locus); methods of using these mice as "indicator mice" to define and visualize angiogenic processes (e.g., tumor angiogenesis and ischemia-associated cardiac neovascularization) or to screen drugs for their angiogenic or anti-angiogenic effects on arteries and arterial cells (e.g., arterial endothelial cells, arterial smooth muscle cells) or veins and venous cells (e.g.,venous endothelial cells, venous smooth muscle cells) in vivo; and cells (e.g., arterial smooth muscle cells), such as immortalized cells, derived from the transgenic mice. The present invention also relates to antibodies which bind an artery-specific Ephrin family ligand (e.g., antibodies which bind EprhinB2 or the extracellular domain of EphrinB2); antibodies which bind a venous-specific Eph family receptor (e.g., antibodies which bind EphB4 or the extracellular domain of EphB4); viral or other vectors which are targeted to arteries and arterial cells (e.g., arterial endothelial cells, arterial smooth muscle cells) or veins and venous cells (e.g.,venous endothelial cells, venous smooth muscle cells) for vessel-specific gene therapy by virtue of their containing and expressing DNA encoding, respectively, an Ephrin family ligand (e.g., EphrinB2) or an Eph family receptor (e.g., EphB4); cDNAs useful for preparing libraries to be screened for additional artery-specific or vein-specific genes (whose gene products, in turn, might be artery- or vein-specific drug targets) and methods of repairing or replacing damaged arteries or veins by transplantation of isolated arterial cells (e.g., arterial endothelial cells, arterial smooth muscle cells) or venous cells, (e.g., venous endothelial cells, venous smooth muscle cells), immortalized cell lines derived from them, or synthetic vessels (e.g., artificially prepared blood vessels) configured from these cells.

The invention also relates to an oligonucleotide encoding a targeting molecule, wherein the targeting molecule is composed of a first nucleic acid which encodes a promoter and/or enhancer region of an arterial-expressed protein (e.g., EphrinB2), and a second nucleic acid which encodes a polypeptide to be targeted to arteries. The invention also relates to a method of inducing expression of such a targeting molecule by administering the targeting molecule to a mammal. In one embodiment, a targeting molecule is administered to a mammal to modulate (e.g., inhibit, promote) angiogenesis.

In another embodiment, the invention is drawn to a method of modifying arteries in a mammal comprising ex vivo therapy. In this embodiment, arterial smooth muscle cells are isolated and introduced with a targeting molecule and then are administered to a mammal.

The invention further relates to a method for modulating angiogenesis (e.g., inhibiting, promoting) in a mammal. In this embodiment, a composition comprising an agent and a substance which binds an arterial smooth muscle cell-specific surface molecule (e.g., EphrinB2), is administered to a mammal. Such a method is appropriate for, e.g., inhibiting tumor growth (e.g., using an agent that inhibits angiogenesis) or promoting wound healing (e.g., using an agent which promotes angiogenesis). In another embodiment, the invention is drawn to a method of modulating (e.g., inhibiting, promoting) angiogenesis comprising administering to a mammal a composition which binds EphrinB2 (e.g., an EphrinB2 antibody or antigen-binding fragment thereof) expressed on arterial smooth muscle cells.

The invention is also drawn to artificially prepared and/or synthetic vessels which comprise arterial smooth muscle cells that express a recombinant nucleic acid which increases expression of EphrinB2.

As described herein and as is known to those of skill in the art, Ephrin family ligands are divided into two subclasses (EphrinA and EphrinB) and Eph family receptors are divided into two groups (EphA and EphB). As is also known, within each subclass or group, individual members are designated by an arabic number. The invention is described herein with specific reference to EphrinB2 and EphB4, however, other Ephrin family ligand-Eph family receptor pairs which show similar artery- and vein-specific expression and their uses are also the subject of this invention. Similar artery- and vein-specific pairs can be identified by methods known to those of skill in the art.

BRIEF DESCRIPTION OF THE DRAWINGS

FIG. 1 is a diagram of the wild type locus of the EphrinB2 gene showing the Exon-1 structure. The filled box represents 5' untranslated region. The hatched box starts at the ATG, and includes the signal sequence. H=HindIII; X=XbaI; N=NcoI; E=EcoRI.

FIG. 2 is a diagram of the targeting vector used to disrupt the EphrinB2 gene.

FIG. 3 is a schematic representation of the mutated EphrinB2 locus.

DETAILED DESCRIPTION OF THE INVENTION

Figure 4:
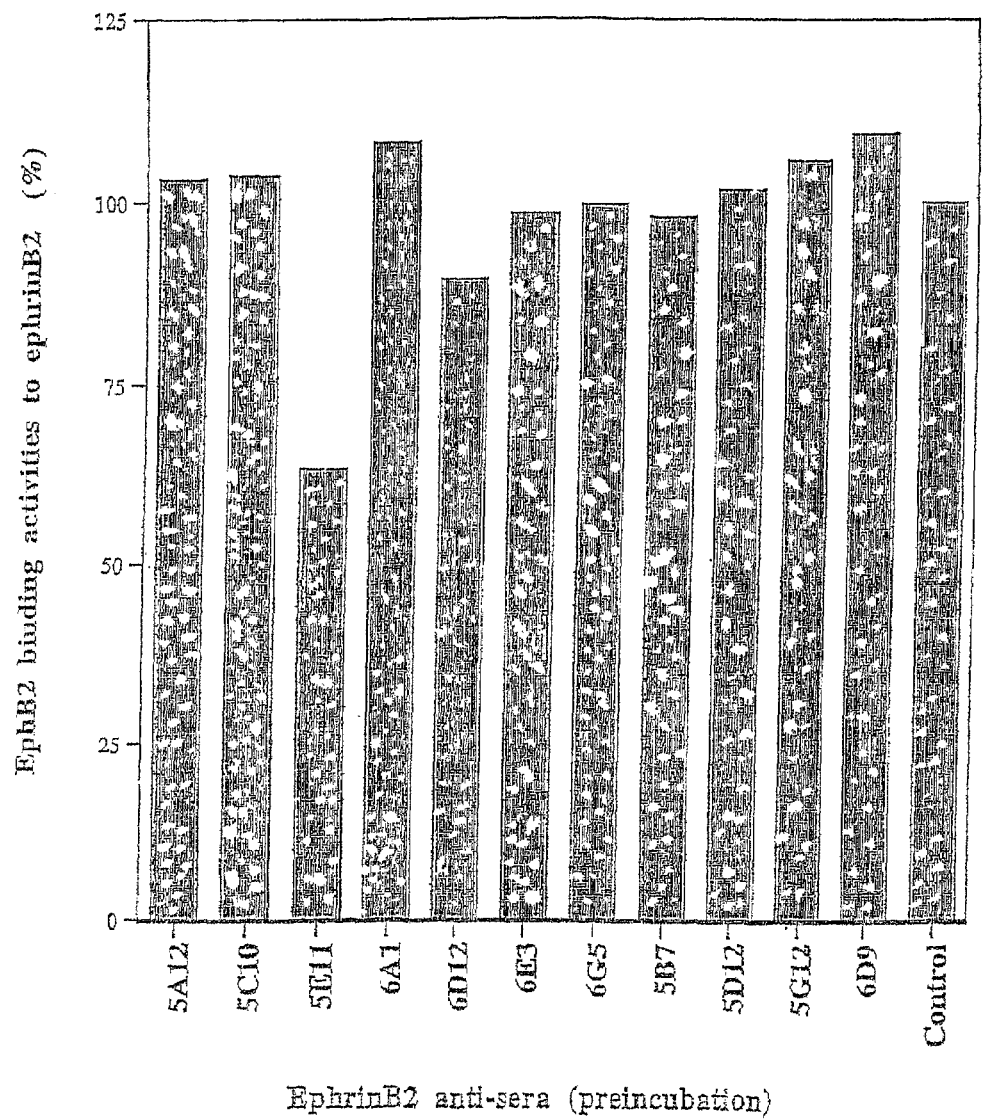
FIG. 4 is a bar graph indicating the binding activity to GPI-ephrin-B2 of EphB2Fc in the presence of hamster anti-ephrin-B2 hybridoma supernatants.

As described herein, it has been shown that arteries and veins are genetically distinct from the earliest stages of embryonic development and that such genetic distinction remains through adulthood. Moreover, reciprocal interactions between arteries and veins are essential for proper vessel formation. This finding not only changes dramatically our view of the basic ontogenetic anatomy of embryonic vasculature, but also provides the means to distinguish between arterial cells (e.g., arterial endothelial cells, arterial smooth muscle cells) and venous cells (e.g., venous endothelial cells, venous smooth muscle cells), both physically and functionally. As a result, means of separating arterial cells and venous cells from one another; of identifing other artery- or vein-specific genes; of assessing the selective effects of drugs or other agents on arteries and arterial cells (e.g., arterial endothelial cells, arterial smooth muscle cells) or veins and venous cells (e.g., venous endothelial cells, venous smooth muscle cells) and, thus, identifying those which are artery- or vein-specific; and of selectively delivering or targeting substances (e.g., an agent, a drug, a nucleic acid, a gene product) to arteries or veins, are now available. In addition, the work described herein makes it possible to modulate (promote (enhance) or inhibit) or control angiogenesis and vasculogenesis and to do so, if desired, in an artery-specific or vein-specific manner.

As described in the examples, a gene which encodes a cell membrane-associated ligand present in the nervous system and the vascular system has been shown to be expressed by arterial cells (e.g., arterial endothelial cells, arterial smooth muscle cells), but not (or not to the same extent) in venous cells (e.g., venous endothelial cells, venous smooth muscle cells), as measured by differential expression or other measures known in the art. Thus, for the first time, a marker found on arterial cells, e.g., arterial endothelial cells, arterial smooth muscle cells, (an artery-specific marker), but not found on venous cells, is available, making it possible to distinguish between arterial cells and venous cells for a variety of purposes, such as further study and understanding of the mechanisms of blood vessel formation; selective targeting of treatments or therapies to arteries and arterial cells (targeting to arteries but not veins or vice versa) and selective modulation (enhancement or inhibition) of formation, growth and survival of arteries and arterial cells and/or veins and venous cells.

In addition, the work presented in the examples demonstrates that reciprocal signaling between arteries and veins is crucial for vessel morphogenesis (e.g., formation of arteries and veins, development of vessels, proliferation of cells). As described, deletion of the ligand-encoding gene in mice prevented the proper development of both arterial and venous vessels. Since the ligand is present on arteries, the occurrence of the venous defect is evidence that veins require a signal from arteries for vessel morphogenesis. Conversely, since the arteries are also defective in the mutant mice, the ligand must have a function in the arterial cells themselves, in addition to its role in signaling to the veins. In view of the fact the ligand present on arterial cells (arterial endothelial cells, arterial smooth muscle cells) is a transmembrane protein, it most likely functions to receive and transduce to arterial cells a reciprocal signal from venous cells.

Specifically, a ligand which is a member of the Ephrin family of Eph family receptor interactive proteins (Eph family of transmembrane ligands) has been shown to be expressed by arterial cells (e.g., arterial endothelial cells, arterial smooth muscle cells) but not at all (or not to the same extent) by venous cells (e.g., venous endothelial cells, venous smooth muscle cells). Thus, it is now possible to distinguish between, and/or target, arteries or arterial cells, as opposed to veins or venous cells, by relying on the presence of an Ephrin family ligand. As described herein, arterial cells (e.g., arterial endothelial cells, arterial smooth muscle cells) have been shown to express EphrinB2 and venous cells (e.g., venous endothelial cells) have been shown to express EphB4, which is a member of the Eph family of receptor protein-tyrosine kinases and a cognate receptor for EphrinB2. EphrinB2 is not expressed on venous cells (e.g., venous endothelial cells, venous smooth muscle cells) and EphB4 is not expressed (or is not expressed to the same extent) on arterial cells (e.g., arterial endothelial cells, arterial smooth muscle cells). This provides a means by which the two cell types can be identified and/or distinguished and, thus, a means by which arterial cells (e.g., arterial endothelial cells, arterial smooth muscle cells) and venous cells (e.g., venous endothelial cells, venous smooth muscle cells) can be, for example, separated from one another, targeted specifically or acted upon in a selective manner (e.g., by an agent, a drug, a nucleic acid and/or a gene product which acts upon one cell type to the exclusion of the other). For example, antibodies that bind to EphrinB2 or to its extracellular domain can be fluorescently labeled and allowed to bind to a mixture of cells, which are then subjected to fluorescent activated cell sorting (FACS) or other suitable method, to select arterial cells from the mixture.

The work described herein, particularly in the examples, refers to EphrinB2 and EphB4. However, any ligand-receptor pair from the Ephrin/Eph family, any other ligand-receptor pair or any gene product produced by one cell type and not the other (e.g., an Ephrin ligand is expressed by arterial smooth muscle cells but not (or not to the same extent) by venous smooth muscle cells and an Eph receptor is expressed by venous smooth muscle cells but not (or not to the same extent) by arterial smooth muscle cells) can be used to distinguish between or identify and, thus, selectively act upon, arterial cells (e.g., arterial smooth muscle cells) or venous cells (e.g., venous smooth muscle cells).

The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the Ephrin-B subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to ephrinA proteins or ephrinB proteins. Receptors which interact preferentially with ephrinA proteins are EphA receptors and those which interact preferentially with ephrinB proteins are EphB receptors.

As used herein, the terms Ephrin and Eph are used to refer, respectively, to ligands and receptors. They can be from any of a variety of animals (e.g., mammals/nonmammals, vertebrates/nonvertebrates, including humans). The nomenclature in this area has changed rapidly and the terminology used herein is that proposed as a result of work by the Eph Nomenclature Committee, which can be accessed, along with previously-used names at web site http://www.eph-nomenclature.com. For convenience, Eph receptors and their respective ligand(s) are given in the Table.

EPH RECEPTORS AND LIGAND SPECIFICITIES

| Eph Receptors | Ephrins |
| --- | --- |
| EphA1 | Ephrin-A1 |
| EphA2 | Ephrin-A3, -A1, A5, -A4 |
| EphA3 | Ephrin-A5, -A2, A3, -A1 |
| EphA4 | Ephrin-A5, -A1, A3, -A2, -B2, -B3 |
| EphA5 | Ephrin-A5, -A1, A2, -A3, -A4 |
| EphA6 | Ephrin-A2, -A1, A3, -A4, -A5 |
| EphA7 | Ephrin-A2, -A3, A1 |
| EphA8 | Ephrin-A5, -A3, A2 |
| EphB1 | Ephrin-B2, -B1, A3 |
| EphB2 | Ephrin-B1, -B2, B3 |
| EphB3 | Ephrin-B1, -B2, B3 |
| EphB4 | Ephrin-B2, -B1 |
| EphB5 | Unknown |
| EphB6 | Unknown |

Ligand specificities are arranged in order of decreasing affinity. Adapted from Pasquale, EB. (1997) Curr. Opin. Cell Biol. 9(5)608.

The work described herein has numerous research and clinical applications, which are discussed below.

As used herein, a transgenic animal (e.g., a mammal such as a mouse, rat, guinea pig, pig, rabbit or sheep) is one which has incorporated into the genome of some or all of its nucleated cells, a genetic alteration which has been introduced into the animal, or at least one of its ancestors, by the manipulations of man. A transgenic mouse, for example, can result from the introduction of DNA into a fertilized mouse ovum or from the introduction of DNA into embryonic stem cells.

One embodiment of the present invention is a transgenic mouse, which because of its particular genotype, expresses only in cells of arteries or only in cells of veins, a gene whose RNA transcript or polypeptide gene product can be detected, for example, by in situ hybridization of RNA, by fluorescence, by detection of enzymatic activity, or by detection of a gene product by antibody binding and a detection system for bound antibodies.

A particular embodiment of the present invention is a transgenic mouse of genotype EphrinB2$^{+/-}$, wherein the "minus" allele denotes an allele in which a naturally-occurring allele has been deleted, modified or replaced with a mutant allele, including a mutant allele which can have an insertion of an indicator gene. Such a "minus" allele can encode an EphrinB2 ligand which has wild type, altered or no ligand function. A mouse of genotype EphrinB2$^{+/tlacZ}$ has been produced as described in Example 1 and used to demonstrate that arterial cells (e.g., arterial endothelial cells, arterial smooth muscle cells) and venous cells (e.g., venous endothelial cells, venous smooth muscle cells) differ genetically from early stages of development through adulthood, and that reciprocal interactions, essential for proper capillary bed formation, occur between the two types of vessels. A transgenic mouse of the same phenotype can be produced by other methods known to those of skill in the art. Such methods are described below using the EphrinB2 gene as an example, but can also be used for any other vein- or artery-specific gene.

For example, it is possible to produce a vector carrying an insertion, a deletion, or one or more point mutations in the EphrinB2 gene. The EprhinB2 transgene can be introduced into the genome, via a vector carrying a mutagenized EphrinB2 allele, e.g., by introducing the transgene into a fertilized ovum, by the method of Wagner et al., U.S. Pat. No. 4,873,191 (1989), or by introducing the transgene into embryonic stem (ES) cells (see, for example, Capecchi, M. R., Science 244:1288–1292, (1989)), or by other suitable methods known to those in the art.

An insertion of DNA used to construct a transgenic knockout mouse can have within it a gene whose presence can be readily tested, such as neo, which confers upon its host cells resistance to G418. It is an advantage of an EphrinB2$^{+/-}$ indicator mouse (e.g., EphrinB2$^{+/tlacZ}$) to be able to express, under the control of the EphrinB2 promoter, an indicator gene. As used herein, an indicator gene can be any gene which is not endogenously expressed by the mouse. A particularly advantageous indicator gene is one which facilitates the detection of EphrinB2 expression, presumably as it is occurring in the wild type allele, by the production of a gene product that is detectable, for example, by its light absorbance properties, its ability to act upon a substrate to yield a detectable product (e.g., a colored product), or its ability to bind to an indicator or dye which is itself detectable.

In one embodiment, the invention is drawn to a transgenic animal which possesses a recombinant nucleic acid encoding an indicator gene within its genome, wherein the indicator gene is expressed in arterial smooth muscle cells but is not expressed in venous smooth muscle cells. Such a recombinant nucleic acid can comprise, for example, a nucleic acid encoding an indicator gene (e.g., lacZ) which is operably linked to a promoter and/or enhancer from an arterial smooth muscle cell specific gene (e.g., an ephrin family ligand such as ephrinB2).

Further, alternative methods are available to produce conditional knockouts or tissue specific knockouts of a gene expressed specifically in veins or in arteries (i.e., a vein-specific or artery-specific gene), for example by a site-specific recombinase such as Cre (acting at loxP site) or FLP1 (acting at FRT site) of yeast.

The bacteriophage P1 Cre-loxP recombination system is capable of mediating loxP site-specific recombination in both ES cells and transgenic mice. The site-specific recombinase Cre can also be used in a predefined cell lineage or at a certain stage of development. See, for example, Gu, H. et al., Science 265:103–106, 1994, in which a DNA polymerase β gene segment was deleted from T cells; see also Tsien, J. Z. et al., Cell 87:1317–1326, 1996, in which Cre/loxP recombination was restricted to cells in the mouse forebrain. The impact of the mutation on these cells can then be analyzed.

The Cre recombinase catalyzes recombination between 34 base pair loxP recognition sequences (Sauer, B. and Henderson, N., Proc. Natl. Acad. Sci. USA 85:5166–5170 (1988)). The loxP sequences can be inserted into the genome of embryonic stem cells by homologous recombination such that they flank one or more exons of a gene of interest (making a "floxed" gene). It is crucial that the insertions do not interfere with normal expression of the gene. Mice homozygous for the floxed gene are generated from these embryonic stem cells by conventional techniques and are crossed to a second mouse that harbors a Cre transgene under the control of a tissue type- or cell type-specific transcriptional promoter. In progeny that are homozygous for the floxed gene and that carry the Cre transgene, the floxed gene will be deleted by Cre/loxP recombination, but only in those cell types in which the Cre gene-associated promoter is active. Thus, for example, a conditional knockout of a gene in arterial cells (as opposed to venous cells) could be generated using a mouse which harbors a Cre transgene under the control of an arterial-specific transcriptional promoter, e.g., EphrinB2. Similarly, a conditional knockout of a gene in venous cells (as opposed to arterial cells) could be generated using a mouse which harbors a Cre transgene under the control of a venous-specific transcriptional promoter, e.g., EphB4.

A gene that encodes a protein which acts to have the effect of mimicking the phenotype caused by mutations in a vein-specific or artery-specific gene can also be used to achieve the same effect as knockouts in vein-specific or artery-specific genes.

A mutation in a gene which encodes a product which prevents binding of ligand to receptor or prevents the functional consequences of such binding and thereby duplicates the phenotype of a vein- or artery-specific gene knockout (e.g., a dominant negative mutant) can be used as an alternative to a gene knockout approach. The mutated gene can be put under the control of a cell type-specific promoter (e.g., an alpha smooth muscle actin (SMA) promoter), a vein-specific promoter (e.g., an ephB4 promoter) and/or an artery-specific promoter (e.g., an ephrinB2 promoter), depending on the tissue-specific gene product whose function is to be inhibited.

In addition, one or more dominant negative alleles of an artery-specific or vein-specific gene can be put under the control of an inducible promoter so that upon induction, the effect of the inhibition of gene function can be studied. A dominant negative mutant can be isolated or constructed using mutagenesis and tested in vivo using a transgenic mouse expressing the desired mutant protein.

Testing to identify the desired mutant or wild type alleles, or for the identification of other alleles, can be done using the polymerase chain reaction (PCR) on isolated genomic DNA with appropriate primers, or by Southern blotting using appropriate hybridization probes, by a combination of these procedures, or by other suitable methods.

In one embodiment, the invention is drawn to a method of identifying arterial smooth muscle cells in a transgenic animal, wherein the transgenic animal possesses a genome comprising a recombinant nucleic acid which encodes an indicator gene inserted in one or more alleles of EphrinB2. Detection of the indicator gene, coupled with detection of a smooth muscle cell-specific protein (e.g., detecting smooth muscle actin (SMA) using an antibody or antigen-binding fragment which binds SMA), on cells is indicative that the cells are arterial smooth muscle cells. Alternatively, one can detect arterial smooth muscle cells using only detection of the indicator gene (i.e., without detection of a smooth muscle cell-specific protein) based on morphological criteria. One of skill in the art can determine which detected cells are, for example, arterial smooth muscle cells as opposed to arterial endothelial cells. Detection of the indicator gene can, for example, comprise staining a tissue sample obtained from a transgenic animal which expresses the indicator gene, with a substance appropriate for detection of expression of the indicator gene. Suitable indicator genes and techniques for detection are described herein and/or are well known in the art.

In addition to the uses of an indicator mouse described in the Examples herein, one use of a mouse having an indicator gene which can mark arterial cells (e.g., arterial endothelial cells, arterial smooth muscle cells) is a method for testing an effect of an agent (e.g., a drug, a nucleic acid, a gene product, a targeting molecule) on growth, development, recruitment and/or proliferation of arteries. The method can comprise administering the agent to a transgenic animal (e.g., a mouse, including an embryo, a neonate, a juvenile, an adult, a wound site, a tumor, an ischemic lesion, an arterial, venous or arteriovenous malformation in any of the preceding) having an indicator gene inserted in a gene specifically expressed in arteries (e.g., EphrinB2), and observing the effect of the agent on the growth, development, recruitment and/or proliferation of the arteries, as compared to the effect in a suitable control mouse having the indicator gene and maintained under identical conditions, but not administered the agent. Similar tests may be performed on an indicator mouse having an indicator gene which marks venous cells (e.g., EphB4). The effect of the agent can be, for example, to promote or to inhibit, growth, development, recruitment and/or proliferation, or to promote aberrant growth, development, recruitment and/or proliferation. In one embodiment, proliferation of arterial smooth muscle cells is modulated (e.g., inhibited, promoted) by administration of the agent. Administration of the agent can be by any suitable route known to those of skill in the art.

An indicator mouse having an indicator gene inserted in a gene specifically expressed in artery cells can be crossed with a mouse of another strain carrying a mutation in a gene which is to be tested for its effect on the growth, development, recruitment and/or proliferation of blood vessels, to allow for easier visualization of the effects of the mutation specifically on arterial cells. In tests similar to those described above, the effect of an agent can be assessed on the mouse which results from this type of cross, to see, for example, whether the effect of the mutation can be alleviated by the agent. In like manner, an indicator mouse having an indicator gene inserted in a gene specifically expressed in venous cells can be used in a cross with a mouse with a mutation whose effect on growth and/or development of veins is to be evaluated, and the resulting hybrid used in studies of veins.

As a result of the work described herein, it is possible to differentiate between arterial cells (arteries) and venous cells (veins) by taking advantage of the presence of an artery-specific or vein-specific gene product on the surface of the cells. Arterial cells and venous cells can each be isolated from cells of other tissue types by, for instance, excision of artery or vein tissue from a sample of mammalian tissue, dissociation of the cells, allowing the cells to bind, under appropriate conditions, to a substance which has some property or characteristic (e.g., a molecule which provides a label or tag, or molecule that has affinity for both the an artery-specific cell surface protein and another type of molecule) that facilitates separation of cells bound to the substance from cells not bound to the substance. This method can be combined with other methods known in the art to further isolate cells. Separation of the cells can take advantage of the properties of the bound substance. For example, the substance can be an antibody (antiserum, polyclonal or monoclonal) which has been raised against a protein specific to arterial cells (or to a sufficiently antigenic portion of the protein) and labeled with a fluorochrome, with biotin, or with another label. Separation of cells bound to the substance can be by fluorescence activated cell sorting (FACS) for a fluorescent label, by streptavidin affinity column for a biotin label, by other affinity-based separation methods, or, for example, by antibody-conjugated magnetic beads or solid supports. "Isolated" as used herein for cells indicates that the cells have been separated from other cell types so as to be a population enriched for a certain cell type, compared to the starting population, and is not limited to the case of a population containing 100% of one cell type.

In one embodiment, the invention is drawn to a method of identifying arterial smooth muscle cells in a mammalian tissue sample comprising contacting the tissue sample with a first composition which binds to EphrinB2 and a second composition which binds to a protein expressed on smooth muscle cells (e.g., smooth muscle actin). Detection of expression of both compositions on a cell is indicative that the cell is an arterial smooth muscle cell. Suitable compositions include antibodies and antigen-binding fragments thereof as well as compositions which have a label conjugated to them, e.g., a fluorescent label, a colorimetric label, an enzyme label, an affinity label, an epitope label, a spin label or a chemiluminescent group.

In another embodiment, arterial smooth muscle cells are isolated by dissociating cells of a tissue sample containing arterial smooth muscle cells and contacting the dissociated cells with both a substance which binds to a cell surface protein expressed on arterial smooth muscle cells and a substance which binds to a cell surface protein expressed on smooth muscle cells. Those cells which bind to both the cell surface proteins are arterial smooth muscle cells and can be separated from those cells that do not bind both cell surface proteins. In one embodiment, one or both of the cell surface proteins are bound to a solid support which facilitates separation of the bound cells. Substances which bind to the cell surface proteins expressed on arterial smooth muscle cells and smooth muscle cells can be, for example, antibodies or antigen-binding fragments, cognate receptors (e.g., Eph family receptors) or cognate ligands (e.g., Ephrin family ligands). In one embodiment, the substance which binds to a cell surface protein expressed on arterial smooth muscle cells is selected from the group consisting of an antibody or antigen-binding fragment which binds EphrinB2 and a soluble Ephrin-B2 binding portion of EphB4. In another embodiment, the substance which binds to a cell surface protein expressed on smooth muscle cells is an antibody or antigen-binding fragment which binds to smooth muscle actin. The invention is also drawn to arterial smooth muscle cells which are isolated using this method, cell lines derived from arterial smooth muscle cells which are isolated using this method and cDNA libraries produced from arterial smooth muscle cells which are isolated using this method.

Other means of separation can exploit, for blood vessel cells bearing an indicator insertion in a gene encoding an artery- or vein-specific protein, the properties of the indicator gene product or portion of fusion protein encoded by the indicator insertion. For example, cells producing an artery- or vein-specific fusion protein with a green fluorescent protein portion or a blue fluorescent protein portion can be separated from non-fluorescent cells using a cell sorter. Cells producing a fusion protein having an artery- or vein-specific protein portion and an indicator protein or portion with binding or enzymatic activity can be detected by enzymatic activity, by the ability of the fusion protein to bind to a fluorescent substrate (e.g., a substrate for $\beta$-galactosidase, a substrate for $\beta$-lactamase), and/or by the ability to produce a fluorescent product in cells.

The isolation of arterial cells (e.g., arterial endothelial cells, arterial smooth muscle cells) and the isolation of venous cells (e.g., venous endothelial cells, venous smooth muscle cells) allows for tests of these cell types in culture to assess the effects of various agents (e.g., drugs, growth factors, ligands, cytokines, members of the Eph and Ephrin families of receptors and ligands, molecules that bind to cell surface proteins, other molecules which can have effects on the growth and development of arteries and veins). One or more of these substances can be added to the culture medium, and the effects of these additions can be assessed (e.g., by measuring growth rate, proliferation and/or viability, using enzyme assays, using assays for the presence of cell surface components, measuring incorporation of labeled precursors into macromolecules such as DNA, RNA or proteins).

Isolated arterial cells (e.g., arterial endothelial cells, arterial smooth muscle cells) or isolated venous cells (e.g., venous endothelial cells, venous smooth muscle cells) can be maintained in artificial growth medium, and an immortalized cell line can be produced from such isolated cell type (i.e., "transformation") by infection with one of any number of viruses (e.g., retroviruses, adenoviruses, by transduction of immortalizing oncogenes such as v-myc, SV40 T antigen, or telomerase plus oncogene) known to effectively transform cells in culture. The virus can be chosen for its species specificity of infectivity (e.g., murine ecotropic virus for mouse cells; amphotropic or pseudotyped viruses for human cells). As an alternative to viral transformation, cells can be maintained in culture by propagating the cells in medium containing one or more growth factors.

Immortalized cell lines derived from either isolated arterial cells (e.g., arterial endothelial cells, arterial smooth muscle cells) or isolated venous cells (e.g., venous endothelial cells, venous smooth muscle cells) can be used to produce cDNA libraries to facilitate study of genes actively expressed in each of these cell types. Further, such cell lines can be used to isolate and identify proteins expressed in the cells, for instance, by purifying the proteins from conditioned growth medium or from the cells themselves.

As one alternative to using immortalized cell lines of arterial or venous origin, cells or cell lines of non-arterial origin or non-venous origin (e.g., smooth muscle cells from other tissues) can be genetically altered (by the introduction of one or more non-endogenously expressed genes) to express an artery-specific or vein-specific cell surface protein, and used in methods to detect and identify substances that interfere with receptor-ligand interaction.

Introduction of one or more genes into a cell line can be, for instance, by transformation, such as by electroporation, by calcium phosphate, DEAE-dextran, or by liposomes, using a vector which has been constructed to have an insertion of one or more genes. See Ausubel, F. M. et al, *Current Protocols in Molecular Biology*, chapter 9, containing supplements through Supplement 40, Fall, 1997, John Wiley & Sons, New York. The introduction of one or more genes to be expressed in a cell line can also be accomplished by viral infection, for example, using retroviral or adenoviral transformation. Viral gene transfer has been used successfully to introduce genes into whole cell populations, thereby eliminating problems associated with clonal variation.

The ability to differentiate and to isolate the cells of veins and arteries allows for a wide variety of applications for a wide variety of purposes. For example, it is now possible to assess the effects of various agents, such as drugs, diagnostic reagents, environmental agents, dietary factors, nucleic acids and gene products, on arteries and/or veins and to determine if the effects observed are common to both types of cells or specific to one cell type.

For example, it can no longer be assumed that angiogenic and anti-angiogenic factors or drugs act equivalently on arterial and venous cells. Isolation of cell types of these tissues, which is made possible by the present work, allows testing of these angiogenic and anti-angiogenic factors for arterial and/or venous specificity, which will provide more selective clinical indications for these drugs. It will also allow the discovery of new artery- or vein-selective drugs, such as by high-throughput screening of immortalized arterial cell lines (e.g., arterial endothelial cells, arterial smooth muscle cells) or venous cell lines (e.g., venous endothelial cells, venous smooth muscle cells). Existing drugs can also be selectively targeted to arteries or veins by using the proteins described herein as targeting devices (e.g., liposomes or viral vehicles having the protein or an extracellular domain portion thereof on the viral surface) to deliver drugs (e.g., chemically coupled drugs) to one type of blood vessel or the other. For example, artery-specific agents can be used to promote collateral growth of arteries to bypass coronary artery occlusions or ischemic lesions. In one embodiment, a drug is selectively delivered to arterial smooth muscle cells in a mammal, by administering a composition which comprises the drug and a substance which binds an arterial smooth muscle cell-specific surface molecule, e.g., an Ephrin family ligand or Eph family receptor. In another embodiment, the substance which binds an arterial smooth muscle cell-specific surface molecule binds to EphrinB2. Agents (e.g., drugs or therapeutic agents) which can be delivered to arterial smooth muscle cells include angiogenic drugs, anti-angiogenic drugs and drugs which inhibit thrombosis, stenosis, restenosis and/or atherosclerotic plaque formation.

In one embodiment, the invention is drawn to a method of modulating (e.g., inhibiting, promoting) angiogenesis comprising administering to a mammal, a composition comprising an agent and a substance which binds an arterial smooth muscle cell-specific surface molecule (e.g., EphrinB2), under conditions appropriate for binding of the substance to the arterial smooth muscle cell-specific surface molecule. Such a method is appropriate, e.g., in inhibiting tumor growth (e.g., using an agent that inhibits angiogenesis) or in promoting wound healing (e.g., using an agent which promotes angiogenesis). Suitable anti-angiogenic and angiogenic agents include those described herein and those well known in the art. In yet another embodiment, the invention is drawn to a method of modulating (e.g., inhibiting, promoting) angiogenesis comprising administering to a mammal a composition which binds EphrinB2 (e.g., an EphrinB2 antibody or antigen-binding fragment thereof) expressed on arterial smooth muscle cells.

Examples of angiogenic factors or drugs include those that are well known in the art, e.g., growth factors, such as basic fibroblast growth factors (b-FGF), endothelial cell growth factors (ECGF), epidermal growth factors (EGF), transforming growth factors (TGF-β), platelet-derived endothelial cell growth factors (PDGF), vascular endothelial cell growth factors (e.g., VEGF-A, VEGF-B, VEGF-C, VEGF-D, PlGF), vascular permeability factors (VPF), angiopoietins (e.g., Ang-1, Ang-4), and the like. Also included are heparin, adenosine and the like.

Examples of anti-angiogenic factors or drugs include agents which inhibit angiogenesis or inhibit the activity of angiogenic factors, such as thalidomide, Angiostatin™, Endostatin™, 2-methoxyestradiol, antagonists of the IL-8 receptor (see, U.S. Pat. No. 6,105,908), angiopoietins (Ang-2, Ang3) and the like.

Examples of other suitable agents which can be targeted to arterial cells include but are not limited to, cyclin G1 mutant polypeptides, p27–p16 chimeric polypeptides, hepatocyte growth factors, herpes simplex virus thymidine kinase polypeptides in the presence of ganciclovir, cytosine deaminase-5-flurocytosine polypeptides, mutant retinoblastoma (Rb) polypeptides (including non-phosphorylatable Rb polypeptides), chimeric pRb2/p130 polypeptides, p21 polypeptides, p27 polypeptides, p53 polypeptides, dominant negative H-ras polypeptides, eNOS polypeptides and 1NOS polypeptides. In addition, antisense nucleic acids, e.g., synthetic double-stranded nucleic acids with high binding affinity for E2F, antisense oligonucleotides to p65 and antisense oligonucleotides to basic fibroblast growth factor (b-FGF) are also suitable agents. Also included are inhibitors of the early coagulation cascade (active site inactivated factor VIIa polypeptides (DEGR-5 VIIa)) and recombinant tissue factor pathway inhibitors (TFPI). Such agents can be delivered as targeting molecules or can be targeted using liposomes (e.g., liposomes comprising an antibody or antigen-binding fragment thereof which binds ephrinB2) or other methods known in the art. Other agents include rapamycin, antioxidants (e.g., Probeol®), glycoprotein IIb/IIa receptor antagonists (e.g., Abciximab®), calcium channel blockers (e.g., Nifedipine®) and nitric oxide donors.

In one embodiment, the invention is an oligonucleotide encoding a targeting molecule which comprises a first nucleic acid sequence comprising a promoter and/or enhancer region of EphrinB2 operably linked to a second oligonucleotide encoding a polypeptide. As used herein, operably linked means that the two nucleic acid sequences are joined such that the first nucleic acid (encoding the promoter and/or enhancer region) induces expression of the second nucleic acid (encoding the polypeptide) in the appropriate tissues and/or at appropriate times. Suitable polypeptides include proteins and functional fragments thereof and include those described herein.

In another embodiment, the invention is a method of inducing expression of a polypeptide in arterial smooth muscle cells comprising administering to a mammal a targeting molecule. Suitable targeting molecules include those described herein and other suitable polypeptides which would be suitable for targeting to arterial smooth muscle cells, and are well known in the art. Suitable methods for administering a targeting molecule to a mammal include administration by viral delivery (e.g., adenoviral delivery, retroviral delivery, lentiviral delivery), naked DNA injection, direct administration using a gene gun, incorporation in liposomes (e.g., cationic liposomes, liposomes expressing an EphrinB2 antibody or antigen-binding fragment thereof), incorporation into a molecular conjugate or via a catheter (see Feldman, L. J., et al. *Cardiovascular Research* 32:194–207 (1996)).

The design of appropriate vectors for expressing a desired polypeptide in arterial smooth muscle cells is known to those of skill in the art (see, e.g., Keogh M-C, et al., *Gene Therapy* 6(4):616–628 (1999)). In addition, the discovery of arterial-specific expression of EphrinB2 also allows for the development of viral vectors (e.g., adenoviral vectors, retroviral vectors, lentiviral vectors) with arterial tropism (i.e., viruses which possess the 5' region (e.g., promoter and/or enhancer regions) of the EphrinB2 gene). Such viruses would target arterial cells (and not venous cells) and would avoid the toxic problems associated with accumulation of virus in the liver.

There are numerous approaches to screening agents for their selective effects (e.g., angiogenic effects, anti-angiogenic effects, anti-thrombotic effects, anti-stenotic and/or anti-restenotic effects, inhibition of formation of atherosclerotic plaques, effects on vasotension) on arteries and/or veins. For example, high-throughput screening of compounds or molecules can be carried out to identify agents or drugs which act selectively on arteries or veins or, in some cases, on both. Test agents to be assessed for their effects on arterial cells (e.g., arterial endothelial cells, arterial smooth muscle cells) or venous cell (e.g., venous endothelial cells, venous smooth muscle cells) can be any chemical agent (e.g., element, molecule, compound) which is made synthetically, made by recombinant techniques or isolated from a natural source. For example, test agents can be peptides, polypeptides, peptoids, peptidomimetics, sugars, hormones, or nucleic acid molecules (including both single-stranded and double-stranded DNA, RNA or antisense nucleic acid molecules). In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically-engineered products isolated from lysates or growth media of cells (e.g., bacterial, animal or plant) or the cell lysates or growth media themselves. Presentation of test compounds to the test system can be in either an isolated form or as mixtures of compounds, especially in initial screening steps.

The compounds or molecules (referred to collectively as agents or drugs) which are screened can be those already known to have angiogenic activity, anti-angiogenic activity, anti-plaque activity and/or vasoactivity, or those of unknown effectiveness. In the case of those agents with known effects, the screening will be useful to identify those agents which act selectively on arterial cells (e.g., arterial smooth muscle cells) or on venous cells (e.g., venous smooth muscle cells). In the case of those agents of unknown effect, screening will be useful to identify new agents which have, for example, angiogenic activity, anti-angiogenic activity, anti-plaque activity, anti-thrombotic activity, anti-stenotic activity, anti-restenotic activity and/or vasoactivity, and to establish the cell type (e.g., arterial smooth muscle cell, venous smooth muscle cell) on which they act. For example, immortalized cell lines of arterial cell types (e.g., arterial endothelial cells, arterial smooth muscle cells) or venous cell types (e.g., venous endothelial cells, venous smooth muscle cells) can be used to screen libraries of compounds to identify drugs with artery- or vein-specific drug effects.

In one embodiment, an assay can be carried out to screen for agents (e.g., drugs) that specifically inhibit binding of an Ephrin ligand to its Eph receptor, such as binding of EphrinB2 to the EphB4 receptor, or vice-versa, by inhibition of binding of labeled ligand- or receptor-Fc fusion proteins to immortalized cells. Alternatively, libraries can be screened to identify members which enhance binding of an Ephrin ligand to its Eph receptor by enhancing binding, for example, of labeled ligand or receptor-Fc fusion proteins to immortalized cells. Agents (e.g., drugs) identified through this screening can then be tested in animal models (e.g., models of cancer and/or tumor formation, models of arterial malformations, models of venous malformations, models of arteriovenous malformations, models of coronary artery disease, models of neovascularization (e.g., corneal micropocket assay), models of wound healing (e.g., cutaneous wound healing)) to assess their activity in vivo.

An agent that inhibits interaction of an artery-specific cell surface molecule (e.g., an arterial endothelial cell- or arterial smooth muscle cell-specific surface molecule) with a vein-specific cell surface molecule (e.g., a venous endothelial cell- or venous smooth muscle cell-specific surface molecule) can be identified by a method in which, for example, the arterial cell-specific surface molecule and the venous cell-specific surface molecule are combined with an agent to be assessed for its ability to inhibit interaction between the cell-specific molecules, under conditions appropriate for interaction between the cell-specific molecules. The cell-specific molecules may be used in the assay such that both are found on intact cells in suspension (e.g., isolated arterial cells (e.g., arterial endothelial cells, arterial smooth muscle cells) or venous cells (e.g., venous endothelial cells, venous smooth muscle cells), immortalized cells derived from these, or cells which have been modified to express an artery- or vein-specific cells surface molecule); one cell type is fixed to a solid support, and the other molecule specific to the other cell type is in soluble form in a suitable solution; or the molecule specific to one cell type is fixed to a solid support while the molecule specific to the other cell type is found free in a solution that allows for interaction of the cell-specific molecules. Other variations are possible to allow for the convenient assessment of the interaction between the two different cell-specific molecules.

In further steps of the assay, the extent to which the cell-specific molecules interact is determined, in the presence of an agent, and in a separate test (control), in the absence of the agent. The extent to which interaction of the cell-specific molecules occurs in the presence and in the absence of the agent to be assessed is compared. If the extent to which interaction of the cell-specific molecules occurs is less in the presence of the agent than in the absence of the agent, the agent is one which inhibits interaction of the arterial cell-specific molecule with the venous cell-specific molecule. If the extent to which interaction of the cell-specific molecules occurs is greater in the presence of the agent than in the absence of the agent, the agent is one which enhances interaction of the arterial cell-specific molecule with the venous cell-specific molecule.

In one embodiment of an assay to identify a substance that interferes with interaction of two cell surface molecules, one specific to artery and the other specific to vein (e.g., binding of a ligand to a receptor that recognizes it; interaction between adhesion proteins; interaction between a cell surface protein and a carbohydrate moiety on a cell surface), samples of cells expressing one type of cell surface molecule (e.g., cells expressing an Eph receptor, such as a vein-derived cell line or other cells genetically manipulated to express an Eph receptor) are contacted with either labeled ligand (e.g., an ephrin ligand, a soluble portion thereof, a soluble fusion protein such as a fusion of the extracellular domain of the ligand and the Fc domain of an IgG molecule) or labeled ligand plus a test compound or group of test compounds. The amount of labeled ligand which has bound to the cells is determined. A lesser amount of label (where the label can be, for example, a radioactive isotope, a fluorescent label, a colorimetric label, an enzyme label, an affinity label (e.g., biotin, avidin), an epitope label or tag (e.g., a hemagglutinin (HA) epitope), a spin label or a chemiluminescent label) in the sample contacted with the test compound(s) is an indication that the test compound(s) interferes with binding. The reciprocal assay using cells expressing a ligand (e.g., an Ephrin ligand or a soluble form thereof) can be used to test for a substance that interferes with the binding of a receptor or soluble portion thereof.

An assay to identify a substance which interferes with interaction between artery-specific and vein-specific cell surface proteins can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

Upon the isolation from a mammal of a gene expressing an artery-specific or a vein-specific protein, the gene can be incorporated into an expression system for production of a recombinant protein or fusion protein, followed by isolation and testing of the protein in vitro. The isolated or purified protein can also be used in further structural studies that allow for the design of agents which specifically bind to the protein and can act as agonists or antagonists of the receptor and/or ligand activity of the protein. In addition, the promoter and/or enhancer of the gene can be used to produce targeting molecules exhibiting artery-specific or vein-specific expression.

In one embodiment, an isolated or purified artery-specific or vein-specific protein can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all of, or a portion of, an artery-specific or a vein-specific protein linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by the insertion of a gene specifically expressed in artery or vein cells or a portion thereof into a suitable expression vector, which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein).

Immobilization can be performed prior to, simultaneous with, or after contacting the fusion protein with compound, as appropriate. Various permutations of the method are possible, depending upon factors such as the compound(s) tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also, Rutter, W. J. et al., U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

An in vivo assay useful to identify drugs which act selectively on arteries or on veins is also available. It is carried out using transgenic animals, such as those described herein, which make it possible to visualize angiogenic processes. For example, an EphrinB2 knockout mouse containing a marker, such as a tau-lacZ insertion, that marks all arteries but not veins, can be used for a variety of in vivo assays. Other marker genes that can be used, for instance, are genes expressing alkaline phosphatase, blue fluorescent protein or green fluorescent protein. The mouse, or the targeted allele it contains, can be used to study angiogenic processes, such as tumor angiogenesis and ischemia-associated cardiac neovascularization, in arteries, independent of veins. For example, as described herein, tumor cells can be implanted in the indicator mouse and arterial vessel growth into the tumor can be visualized by lacZ staining. Alternatively, mice bearing the targeted allele can be crossed with a mouse model of another condition, such as vascular degeneration or neovascularization, and then can be visualized. Neovascularization can also be studied, for example, using a corneal micropocket assay or a cutaneous wound healing model as described herein, or other suitable model. The arterial-specific aspects of the process can be visually monitored by lacZ staining. An indicator of this type can also be used to assess drugs or agents for their angiogenic effects, anti-angiogenic effects, anti-plaque effects and/or effects on vasoactivity.

A gene product produced specifically by arterial cells (e.g., arterial endothelial cells, arterial smooth muscle cells) and not by other cell types allows for the specific targeting of agents (e.g., drugs, diagnostic agents, tagging labels, histological stains, imaging agents or other substances) specifically to arteries. In an analogous manner, a gene product identified as produced specifically by venous cells (e.g., venous endothelial cells, venous smooth muscle cells) and not detectably produced by other cell types allows for the specific targeting and delivery of agents (e.g., drugs, diagnostic agents, tagging labels, histological stains, imaging agents or other substances specifically) to veins. The following description of targeting vehicles, targeted agents and methods is presented using EphrinB2 as an illustration of a gene product produced by arterial cells (e.g., arterial endothelial cells, arterial smooth muscle cells) and not at all or to the same extent by vein cells and EphB4 as an illustration of a gene product produced by venous cells (e.g., venous endothelial cells) and not at all or to same extent by arterial cells. However, this description applies equally well to other artery-specific and vein-specific gene products that can be used to identify these tissue types.

The differential expression of EphrinB2 in arteries and of EphB4 in veins allows for the specific targeting of agents (e.g., drugs, diagnostic agents, imaging agents, or other substances) to the cells of arteries (e.g., arterial endothelial cells, arterial smooth muscle cells) or of veins (e.g., venous endothelial cells, venous smooth muscle cells). A targeting vehicle can be used for the delivery of such a substance. Targeting vehicles which bind specifically to EphrinB2 or to EphB4 can be linked to a substance to be delivered to the cells of arteries or veins, respectively. The linkage can be via one or more covalent bonds, by high affinity non-covalent bonds or by other means known to those of skill in the art. A targeting vehicle can be an antibody or antigen-binding fragment thereof, for instance, or another compound which binds either to EphrinB2 or to EphB4 with high specificity. Another example is an aqueously soluble polypeptide having the amino acid sequence of the extracellular domain of EphB4, or a sufficient antigenic portion of the extracellular domain (or a polypeptide having an amino acid sequence conferring a similar enough conformation to allow specific binding to EphrinB2), which can be used as a targeting vehicle for delivery of substances to EphrinB2 in arteries (e.g., arterial endothelial cells, arterial smooth muscle cells). Similarly, a soluble polypeptide having the amino acid sequence of the extracellular domain of EphrinB2 or a sufficient antigenic portion of the extracellular domain (or a polypeptide having an amino acid sequence conferring a similar enough conformation to allow specific binding to EphB4), can be used to target substances to EphB4 in veins.

Targeting vehicles specific to an artery-specific Ephrin ligand (e.g., EphrinB2) or to a vein-specific Eph receptor (e.g., EphB4) have in vivo (e.g., therapeutic and diagnostic) applications. For example, an antibody which specifically binds to EphrinB2 or another artery-specific protein, can be conjugated to an agent or drug to be targeted to arteries (e.g., a therapeutic, such as an anti-plaque agent, an angiogenic agent, an angiogenic agent). Alternatively, an antibody which specifically binds to EphB4 can be used to target an agent or drug to veins (e.g., a therapeutic, such as an anti-plaque agent, an angiogenic agent, an angiogenic agent). A substance (e.g., a radioactive label, a fluorescent label, a colorimetric label, an enzyme label, an affinity label (e.g., biotin, avidin), an epitope label (tag)(e.g., a hemagglutinin (HA) epitope), a spin label or a chemiluminescent group) which can be detected (e.g., a label) in vivo can also be linked to a targeting vehicle which specifically binds to an artery-specific Ephrin ligand (e.g., EphrinB2) and the conjugate can be used as a labeling agent to identify arteries. Similarly, a detectable label can be linked to a targeting vehicle which specifically binds a vein-specific Eph receptor (e.g., EphB4) to identify veins. Alternatively, targeting molecules, which express a polypeptide under the control of an arterial-specific (e.g., EphrinB2) promoter and/or enhancer can be used in in vivo therapeutic and diagnostic applications Targeting vehicles specific to EphrinB2 or to EphB4 find further applications in vitro. For example, an EphB4-specific targeting vehicle, such as an antibody (a polyclonal preparation or monoclonal antibody) which specifically binds EphB4, can be linked to a substance which can be used as a stain for a tissue sample (e.g., horseradish peroxidase) to provide a method for the identification and/or treatment of veins in a sample. Likewise, an antibody which specifically binds to EphrinB2 or to the extracellular domain of EphrinB2 can be used in the identification and/or treatment of arteries. For instance, in a biopsied tissue sample, as from a tumor, or from an arterial, venous or arteriovenous malformation in a child or adult, antibody to EphrinB2 or to the extracellular domain of EphrinB2 can be used to identify artery tissue and to distinguish it from vein tissue.

To treat malformed, painful or cosmetically undesirable veins, an agent which acts against them (e.g, a sclerosing agent (e.g., ethanol), an anti-angiogenic factor) can be linked to an EphB4-specific vehicle for local administration to the veins. For example, an anti-angiogenic factor which is linked to EphB4 or a portion thereof, can be injected into varicose veins, venous malformations or arteriovenous malformations. Alternatively, such a targeting vehicle can be administered using parenteral administration. Parenteral administration, in addition to intravenous injection, can also include, for example, intramuscular, intraarticular, intraarterial, intrathecal, subcutaneous, or intraperitoneal administration. Other suitable modes of administration include, for example, oral administration (e.g., dietary administration, capsules, suspensions, tablets), inhalation (e.g., intrabronchial, intranasal, oral inhalation or intranasal drops), transdermal administration, topical administration or rectal administration. Administration can be local or systemic, and the preferred mode of administration can vary depending upon the particular agent (e.g., targeting vehicle), however, parenteral administration is generally preferred.

Suitable anti-angiogenic factors include agents which inhibit angiogenesis or inhibit the activity of angiogenic factors, such as thalidomide, Angiostatin™, Endostatin™, 2-methoxyestradiol, antagonists of the IL-8 receptor (see e.g., U.S. Pat. No. 6,105,908) and the like. Other therapeutic agents which can be linked to the artery-specific and/or vein-specific proteins of the invention include, for example, antiviral agents (e.g., acyclovir, ganciclovir, famciclovir, penciclovir, valacyclovir, vidarabine, foscarnet, indinavir), antibacterial agents (e.g., antibiotics (e.g., erythromycin, penicillin, tetracycline, ciprofloxacin, norfloxacin, flurazolidone, azithromycin, chloramphenicol), sulfonamides, quinalones), methotrexate, anti-inflammatory agents (e.g., nonsteroidal anti-inflammatory agents, such as aspirin, ibuprofen, naproxen, lysofylline, inhibitors of cyclooxygenase-2), cytokines (e.g., TGFβ), immunosuppressive agents, such as, calcineurin inhibitors (e.g., cyclosporin A, FK-506), IL-2 signal transduction inhibitors (e.g., rapamycin), glucocorticoids (e.g., prednisone, dexamethasone, methylprednisolone), nucleic acid synthesis inhibitors (e.g., azathioprine, mercaptopurine, mycophenolic acid), and antibodies to lymphocytes and antigen-binding fragments thereof (e.g., OKT3, anti-IL2 receptor), disease modifying anti-rheumatic agents (e.g., D-penicillamine, sulfasalazine, chloroquine, hydroxychloroquine) and antibodies, such as antibodies that bind chemokines, cytokines (e.g., anti-TNFα) or cell adhesion molecules (e.g., anti-CD11/CD18).

Targeted agents directed to either an artery-specific Ephrin family ligand (e.g., EphrinB2) or a vein-specific Eph family receptor (e.g., EphB4) can also be used when it is desired to produce an effect on both arteries and veins. For example, limited amounts of targeted agents comprising an anti-angiogenic drug and a targeting vehicle to either EphrinB2, EphB4, or both, can be administered locally to sites of angiogenesis, such as sites of tumor formation or sites of undesirable neovascularization (pathogenic neovascularization) where it is desired to inhibit the growth of blood vessels. As used herein, "pathogenic neovascularization" refers to (i) the proliferation and/or formation of blood vessels in tissue not normally containing them; (ii) the proliferation of blood vessels of a different kind than are normally found in a tissue; and (iii) the proliferation of blood vessels beyond the amount typically present in a tissue (hypervascularization). Pathogenic neovascularization includes angiogenesis associated with cancers (e.g., tumor formation and growth and/or metastasis), retinopathy (e.g., retinopathy of prematurity, diabetic retinopathy), retinal vein occlusion, macular degeneration (e.g., age-related macular degeneration), neovascular glaucoma, hemangiomas, inflammatory arthritis (e.g., rheumatoid arthritis) and psoriasis.

Alternatively, targeted agents comprising an angiogenic drug and a targeting vehicle to either EphrinB2, EphB4, or both, can be administered locally to sites or to areas in which increased vascularization is desired to enhance growth or establishment of blood vessels (e.g., after transplantation, for wound healing). Suitable angiogenic factors or drugs include agents that are well known in the art, e.g., growth factors, such as basic fibroblast growth factors (b-FGF), endothelial cell growth factors (ECGF), epidermal growth factors (EGF), transforming growth factors (TGF-β), platelet-derived endothelial cell growth factors (PDGF), vascular endothelial cell growth factors (VEGF), vascular permeability factors (VPF), and the like. Also included are heparin, adenosine and the like.

Substances that act as agonists or antagonists of an artery-specific Ephrin family ligand (e.g., EphrinB2) or a vein-specific Eph family receptor (e.g., EphB4) can be used as angiogenic or anti-angiogenic agents. Agents (e.g., drugs) that target these molecules will selectively influence arterial and venous angiogenesis. For example, antibodies (e.g., polyclonal or monoclonal antibodies) to EphrinB2 or EphB4 can serve as artery- or vein-specific angiogenic or anti-angiogenic agents. Drugs that interfere with EphrinB2 function (for instance, blocking antibodies) can be used in anti-angiogenic methods of therapy (e.g., to inhibit tumor growth). As can be concluded from the studies described herein and from the phenotype of the EphrinB2$^{tlacZ}$/EphrinB2$^{tlacZ}$ mutant mice, antagonists of EphrinB2 and/or antagonists of EphB4 will inhibit angiogenesis. Agents which are agonists of both EphrinB2 and EphB4 will promote angiogenesis.

In another example, soluble agonists which comprise the extracellular domain of an Ephrin family ligand or the extracellular domain of an Eph family receptor can be produced. In one embodiment, the extracellular domain of an Ephrin family ligand or the extracellular domain of an Eph family receptor is fused to the Fc domain of a human immunoglobulin (e.g., an IgG). For example, an EphB4 or an EphrinB2 hybrid protein in which the extracellular domain of the membrane protein is fused to the Fc domain of a human IgG antibody can be used (Wang, H. U. and D. J. Anderson, *Neuron* 18:383–396 (1997)). For example, Stein et al. describe experiments concerning responses of cells to clustered Ephrin-B1/Fc fusion proteins (Stein, E. et al., *Genes and Dev.* 12:667–678 (1998)). Clustering of these hybrid molecules with anti-human Fc antibodies generates soluble agonists: Ephrin-derived "ligand-bodies" for Eph receptors, and conversely, Eph-derived "receptor bodies" for Ephrins. Non-clustered forms of these hybrid molecules can be used as antagonists.

A further application of isolated arterial cells (e.g., arterial endothelial cells, arterial smooth muscle cells) and isolated venous cells (e.g., venous endothelial cells, venous smooth muscle cells) is the genetic alteration of the isolated cells and the administration of these cells, preferably intravenously, to the host mammal from which the cells were isolated, or into another compatible host, where the cells can be incorporated into a blood vessel of the appropriate type. In this way, the effects of a genetic defect which is manifested in arteries and/or in veins can be ameliorated. It has been demonstrated that circulating endothelial cell progenitors can migrate to sites of neovascularization and be incorporated into blood vessels (Asahara et al., *Science* 275:964–967 (1997)).

The introduction of a gene (for example, an endogenous gene that has been altered or a gene originally isolated from a different organism) into cells can be accomplished by any of several known techniques. For example, suitable techniques include but are not limited to, vector-mediated gene transfer (e.g., as by amphotropic retroviruses), calcium phosphate or liposome fusion. Other suitable methods are described herein or are well known to those of skill in the art.

A gene intended to have an effect on arteries or veins in a host mammal can be delivered to isolated artery cells or isolated vein cells by the use of viral vectors comprising one or more nucleic acid sequences encoding the gene of interest. Generally, the nucleic acid sequence has been incorporated into the genome of the viral vector. In vitro, the viral vector containing the nucleic acid sequences encoding the gene can be contacted with a cell and infection can occur. The cell can then be used experimentally to study, for example, the effect of the gene on the growth of artery or vein cells in vitro or the cells can be implanted into a patient for therapeutic use. The cells to be altered by introduction or substitution of a gene can be present in a biological sample obtained from the patient and used in the treatment of disease, or can be obtained from cell culture and used to dissect developmental pathways of arteries and/or veins in in vivo and/or in vitro systems.

After contact with the viral vector comprising a nucleic acid sequence encoding the gene of interest, the treated artery or vein cells can be returned or re-administered to a patient according to methods known to those practiced in the art. Such a treatment procedure is sometimes referred to as ex vivo treatment. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature* 310:476 (1984); Dick, et al., *Cell* 42:71 (1985); Keller, et al., *Nature* 318:149 (1985) and Anderson, et al., U.S. Pat. No. 5,399,346 (1994).

Generally, viral vectors which can be used therapeutically and experimentally are known in the art. Examples include the vectors described by Srivastava, A., U.S. Pat. No. 5,252,479 (1993); Anderson, W. F., et al. U.S. Pat. No. 5,399,346 (1994); Ausubel et al., "Current Protocols in Molecular Biology", John Wiley & Sons, Inc. (1998). Suitable viral vectors for the delivery of nucleic acids to cells include, for example, replication defective retroviruses, adenoviruses, parvoviruses (e.g., adeno-associated viruses), and coronaviruses. Examples of retroviruses include but are not limited to, avian leukosis-sarcoma viruses, mammalian C-type viruses, B-type viruses, lentiviruses (Coffin, J. M., "Retroviridae: The Viruses and Their Replication", In: *Fundamental Virology*, Third Edition, B. N. Fields, et al., eds., Lippincott-Raven Publishers, Philadelphia, Pa., (1996)). The mechanism of infectivity depends upon the viral vector and target cell. For example, adenoviral infectivity of HeLa cells occurs by binding to a viral surface receptor, followed by receptor-mediated endocytosis and extrachromasomal replication (Horwitz, M. S., "Adenoviruses" In: *Fundamental Virology*, Third Edition, B. N. Fields, et al., eds., Lippincott-Raven Publishers, Philadelphia, Pa., (1996)).

In one embodiment, the invention is drawn to a method of diagnosing a tumor (e.g., tumor growth, tumor development) or active angiogenesis comprising detecting expression of high levels of EphrinB2 in circulating blood vessels (e.g., obtained from a mammal, such as a human). In this embodiment, expression of EphrinB2, which is highly expressed in proliferating tumor cells, is detected in circulating blood vessels and is diagnostic of the presence of a tumor, tumor growth and/or tumor development. Unlike non-proliferating blood vessels which do not express and shed EphrinB2, proliferating tumor cells express very high levels of EphrinB2 which can be detected in a sample of blood. Expression of EprinB2 is compared to a suitable control, e.g., a blood sample obtained from a mammal (e.g., a human) which does not have tumors and/or cancerous cells. Thus, in this embodiment, ephrinB2 can act as a surrogate marker for tumor growth, much as PSA does for prostrate cancer. In addition, the method can also be used to assess efficacy of treatment or therapy. In this embodiment, expression of EphrinB2 in a sample of blood from a mammal (e.g., a human) having a tumor prior to treatment is compared with expression of EphrinB2 after treatment. A decrease in the expression of EphrinB2 is indicative of efficacy.

In another embodiment, the invention is drawn to artificially prepared vessels which comprise arterial smooth muscle cells, wherein the arterial smooth muscle cells possess a recombinant nucleic acid which increases expression of ephrinB2 above endogenous levels. Smooth muscle cells provide structure, strength, and sufficient mechanical integrity to allow tolerance of systemic arterial pressures (Niklason, L. E., et al., *Science* 284:489–493 (1999); Niklason, L. E. et al., *J. Vasc. Surg.* 33:628–638 (2001)). Thus, expression of EphrinB2 in artificial blood vessels or smooth muscle cells isolated as described herein or as known in the art (Niklason, L. E., et al., *Science* 284:489–493 (1999); Niklason, L. E. et al., *J. Vasc. Surg.* 33:628–638 (2001)), can provide structural and mechanical support for engineered vessels. Thus, expression of EphrinB2 can overcome some of the problems associated with current engineered vessels (e.g., lack of strength, lack of structural integrity).

The present invention is illustrated by the following examples, which are not intended to be limiting in any way. The teachings of all publications cited herein are incorporated herein by reference in their entirety.

EXAMPLES

Experimental Procedures

The following experimental procedures were used in the examples which follow.

Targeted Disruption of the EphrinB2 Gene

A 200 base pair probe starting from the ATG of the mouse EphrinB2 gene (Bennett, B. D., et al., *Proc. Natl. Acad. Sci. USA* 92:1866–1870 (1995)) was used to screen a 129SVJ genomic library (Stratagene, La Jolla, Calif.). Analysis of several overlapping clones revealed that the first exon, including the signal sequence, ends at 131 base pairs after the ATG. Further phage analysis and library screens revealed that the rest of the EphrinB2 gene was located at least 7 kb downstream from the first exon. To construct a targeting vector (FIG. 2), a 3 kb XbaI-NcoI fragment whose 3' end terminated at the ATG was used as the 5' arm. A 5.3 kb Tau-lacZ coding sequence (Mombaerts, P., et al., *Cell* 87:675–686 (1996)) was fused in frame after the ATG start codon. The PGKneo gene (Ma, Q., et al., *Neuron* 20:469–482 (1998)) was used to replace a 2.8 kb intronic sequence 3' to the first exon. Finally, a 3.2 kb downstream EcoRI-EcoRi fragment was used as the 3' arm. Normal (6 kb) and targeted (9 kb) loci are distinguished by HindIII digestion when probed with a 1 kb HindIII-XbaI genomic fragment. Electroporation, selection and blastocyst-injection of AB-1 ES cells were performed essentially as described (Ma, Q., et al. *Neuron* 20:469–482 (1998)), with the exception that the FIAU-selection step was omitted. ES cell targeting efficiency via G418 selection was 1 out of 18 clones. Germline transmission of the targeted EphrinB2 locus (FIG. 3) in heterozygous males was confirmed by Southern blotting of tail DNA of adult mice, using a 1 kb HindIII-XbaI probe. Subsequent genotyping was done by genomic PCR. Synthetic oligonucleotide primers for Neo are:

5'-AAGATGGATTGCACGCAGGTTCTC-3' (SEQ ID NO. 1) and

5'-CCTGATGCTCTTCGTCCAGATCAT-3' (SEQ ID NO. 2). Synthetic oligonucleotide primers for the replaced intronic fragment are:

5'-AGGACGGAGGACGTTGCCACTAAC-3' (SEQ ID NO. 3) and

5'-ACCACCAGTTCCGACGCGAAGGGA-3' (SEQ ID NO. 4).

LacZ, PECAM-1, and Histological Staining

Embryos and yolk sacs were removed between E7.5 and E10.0, fixed in cold 4% paraformaldehyde/PBS (phosphate-buffered saline) for 10 minutes, rinsed twice with PBS, and stained for 1 hour to overnight at 37° C. in X-gal buffer (1.3 mg/ml potassium ferrocyanide, 1 mg/ml potassium ferricyanide, 0.2% Triton X-100, 1 mM MgCl$_2$, and 1 mg/ml X-gal (5-bromo-4-chloro-3-indolyl-β-D-galactopyranoside) in PBS, pH 7.2). LacZ-stained embryos were post-fixed and photographed, or sectioned on a cryostat after embedding in 15% sucrose and 7.5% gelatin in PBS. Procedures for whole mount or section staining with anti-PECAM-1 antibody (clone MEC 13.3, Pharmingen, San Diego, Calif.) were done essentially as described (Ma et al. *Neuron* 20:469–482 (1998); Fong et al., *Nature* 376:66–70 (1995)). Horseradish peroxidase-conjugated secondary antibodies were used for all PECAM-1 stainings. LacZ-stained yolk sacs were sectioned in gelatin and then subjected to hematoxylin counterstaining using standard procedures.

In Situ Hybridization

In situ hybridization on frozen sections was performed as previously described (Birren et al. *Development* 119:597–610 (1993)). Whole-mount in situ hybridization followed a protocol by Wilkinson, D. G. (Whole-mount in situ hybridization of vertebrate embryos. pp. 75–83 In: In Situ Hybridization: A Practical Approach (ed. D. G. Wilkinson) *IRL Press*, Oxford :75–83 (1992)). Bluescript vectors (Stratagene, La Jolla, Calif.) containing cDNAs for EphB2/Nuk and EphB4/Myk-1 were generated as described (Wang, H. U. and Anderson, D. J. *Neuron* 18:383–396 (1997)).

Example 1

Targeted Mutagenesis of EphrinB2 in Mice

Targeted disruption of the EphrinB2 gene was achieved by homologous recombination in embryonic stem cells. The targeting strategy involved deleting the signal sequence and fusing a tau-lacZ indicator gene in frame with the initiation codon. The expression pattern of β-galactosidase in heterozygous (EphrinB2$^{tlacZ/+}$) embryos was indistinguishable from that previously reported for the endogenous gene (Bennett, B. D. et al. *Proc. Natl. Acad. Sci. USA* 92: 1866–1870 (1995); Bergemann, A. D. et al. *Mol. Cell Bio.* 1995:4921–4929 (1995); Wang, H. U. and Anderson, D. J. *Neuron* 18:383–396 (1997)). While prominent expression was detected in the hindbrain and somites, lower levels were observed in the aorta and heart as early as E8.25. Expression in the yolk sac was first detected at E8.5. Heterozygous animals appeared phenotypically normal. In homozygous embryos, growth retardation was evident at E10 and lethality occurred with 100% penetrance around E11. No expression of endogenous EphrinB2 mRNA was detected by in situ hybridization, indicating that the mutation is a null. Somite polarity, hindbrain segmentation, and the metameric patterning of neural crest migration (in which EphrinB2 and related ligands have previously been implicated (see, Xu, W. et al. *Development* 121:4005–4016 (1995); Wang, H. U. and Anderson, D. J. *Neuron* 18:383–396 (1997); Krull, C. E. et al. *Curr. Biol.* 7:571–580 (1997); Smith, A. et al. *Curr. Biol.* 7:561–570 (1997)) appeared grossly normal in homozygous mutant embryos.

Example 2

Reciprocal Expression Pattern of EphrinB2 and EphB4 in Arteries and Veins

The enlarged heart observed in dying mutant embryos prompted examination of the expression of EphrinB2$^{tlacz}$ in the vascular system in detail. Expression was consistently observed in arteries but not veins. In the yolk sac, for example, the posterior vessels connected to the vitelline artery, but not the vitelline vein, expressed the gene, as detected by lacZ staining. In the trunk, labeling was detected in the dorsal aorta, vitelline artery, umbilical artery and its allantoic vascular plexus, but not the umbilical, anterior and common cardinal veins (the umbilical vein was labeled with anti-PECAM-1 antibody). In the head, labeling was detected in branches of the internal carotid artery, but not in those of the anterior cardinal vein. In situ hybridization with EphrinB2 cDNA probes confirmed that the selective expression of tau-lacZ in arteries correctly reflected the pattern of expression of the endogenous gene. Examination of the expression of the four EphB family genes, as well as EphA4/Sek1, which is a receptor for EphrinB2 (Gale, N. W. et al., *Neuron* 17:9–19 (1996)), revealed complementary expression of EphB4 in veins but not arteries, including the vitelline vein and its branches in the anterior portion of the yolk sac.

Example 3

Vasculogenesis Occurs Normally in EphrinB2 Mutant Embryos

The formation of the major vessels in the trunk was unaffected by the lack of EphrinB2, as examined by lacZ and PECAM-1 double staining of 9 somite embryos. Expression of EphrinB2-lacZ was seen in the dorsal aorta and vitelline artery, but not the umbilical and posterior cardinal veins. The dorsal aorta, vitelline artery, posterior cardinal and umbilical veins, for example, formed, although some dilation and wrinkling of the vessel wall was observed. Similarly, the intersomitic vessels originating from the dorsal aorta formed at this stage. Between E8.5 and E9.0, the primitive endocardium appeared only mildly perturbed in EphrinB2 mutants, while a pronounced disorganization was apparent at E10. Red blood cells developed and circulated normally up to E9.5 in both the mutant yolk sac and embryo proper.

Example 4

Extensive Intercalation of Yolk Sac Arteries and Veins Revealed by EphrinB2 Expression In the yolk sac, the vitelline artery and its capillary network occupy the posterior region, and the vitelline vein and its capillaries the anterior region. At E8.5, a stage at which the primary capillary plexus has formed but remodeling has not yet occurred, asymmetric expression of EphrinB2-taulacZ in heterozygous embryos was evident at the interface between the anterior and posterior regions. Apparently homotypic remodeling of β-galactosidase$^+$ arterial capillaries into larger, branched trunks clearly segregated from venous vessels was evident between E9.0 and E9.5. At this stage, expression of the receptor EphB4 was clearly visible on the vitelline veins but not arteries. Thus, arterial and venous endothelial capillaries are already molecularly distinct following vasculogenesis and prior to angiogenesis.

While textbook diagrams (Carlson, B. M. *Patten's Foundations of Embryology* (1981)) of the yolk sac capillary plexus depict a non-overlapping boundary between the arterial and venous capillary beds, expression of EphrinB2-taulacZ allowed detection of a previously-unrecognized extensive intercalation between arteries and veins across the entire anterior-posterior extent of the yolk sac; this was observed in the heterozygote, but not in the homozygote. Double-labeling for PECAM-1 and β-galactosidase revealed that the interface between the arteries and veins occurs between microvessel extensions that bridge larger vessels interdigitating en passant.

Example 5

Disrupted Angiogenesis in the Yolk Sac of EphrinB2$^{tlacZ}$/EphrinB2$^{tlacZ}$ Embryos Defects in yolk sac angiogenesis were apparent by E9.0 and obvious at E9.5. There was an apparent block to remodeling at the capillary plexus stage, for both arterial vessels, as revealed by β-galactosidase staining, and venous vessels in the anterior region of the sac, as revealed by PECAM-1 staining. Thus, disruption of the EphrinB2 ligand gene caused both a non-autonomous defect in EphB4 receptor-expressing venous cells, and an autonomous defect in the arteries themselves.

This defect was accompanied by a failure of intercalating bi-directional growth of arteries and veins across the anterior-posterior extent of the yolk sac, so that an interface between EprhinB2-expressing and non-expressing zones at the midpoint of the sac was apparent. Small patches of lacZ expression, however, were occasionally visible within the anterior venous plexus, suggesting that some arterial endothelial cells may have become incorporated into venous capillaries. These observations imply a close relationship between the remodeling of the capillary plexus into larger vessels and the intercalating growth of these vessels. The large β-galactosidase$^+$ vitelline arteries, as well as vitelline veins present at the point of entry to the yolk sac of the embryo-derived vasculature, appeared unperturbed in the mutant, however. This is consistent with the observation that the mutation does not affect formation of the primary trunk vasculature. It also argues that the yolk sac phenotype is due to a disruption of intrinsic angiogenesis and is not a secondary result of a failure of ingrowth of embryo-derived vessels.

Histological staining (hematoxylin) of sectioned yolk sacs revealed an accumulation of elongated support cells (mesenchymal cells or pericytes) in close association with the endothelial vessels at E10 and E10.5. In mutant yolk sacs, these support cells appeared more rounded, suggesting a defect in their differentiation. Moreover, in contrast to heterozygous yolk sacs, where vessels of different diameters began to appear at E9.5 and vessel diameter increased through E10.5, capillary diameter appeared relatively uniform and did not increase with age in the mutants. At E10.5, arteries appear dilated, as if fusion of vessels occurred without encapsulation by support cells. The mutant capillaries also failed to delaminate from the basal endodermnal layer.

Example 6

Absence of Internal Carotid Arterial Branches and Defective Angiogenesis of Venous Capillaries in the Head of Mutant Embryos Similar to the yolk sac phenotype, the capillary bed of the head appeared dilated in the mutant, and apparently arrested at the primary plexus stage. Staining for β-galactosidase revealed that the anterior-most branches of the internal carotid artery failed to develop in the mutant. Unlike the case in the yolk sac, therefore, the malformed capillary beds must be entirely of venous origin. The anterior branches of the anterior cardinal vein formed, however, although they were slightly dilated. Taken together, these data indicate that in the head, venous angiogenesis is blocked if the normal interaction with arterial capillaries is prevented. The angiogenic defects observed in the head and yolk sac are unlikely to be secondary consequences of heart defects (see below), since they are observed starting at E9.0 and the embryonic blood circulation appears normal until E9.5.

Example 7

EphrinB2-dependent Signaling Between Endocardial Cells is Required for Myocardial Trabeculae Formation Examination of ligand and receptor expression in wild-type hearts revealed expression in the atrium of both EphrinB2 (as detected by lacZ staining) and EphB4 (as detected by in situ hybridization). Expression of both ligand and receptor was also detected in the ventricle in the endocardial cells lining the trabecular extensions of the myocardium. Double-labeling experiments suggested that the ligand and receptor are expressed by distinct but partially overlapping cell populations, although the resolution of the method does not permit us to distinguish whether this overlap reflects co-expression by the same cells, or a close association of different cells. In any case, expression of EphrinB2 and EphB4 does not define complementary arterial (ventricular) and venous (atrial) compartments of the heart, unlike the extra-cardiac vasculature.

Heart defects commenced at E9.5 and were apparent in mutant embryos at E10 both morphologically and by whole-mount PECAM-1 staining. Sections revealed an absence of myocardial trabecular extensions, although strands of EphrinB2-expressing endocardial cells were still visible. Thus, mutation of the ligand-encoding gene caused a non-autonomous defect in myocardial cells, similar to the effect of a mutation in the neuregulin-1 gene (Meyer, D. and Birchmeier, C, *Nature* 378:386–390 (1995)). Paradoxically, however, in this case the EphB4 receptor is expressed not on myocardial cells, as is the case for the neuregulin-1 receptors erbB2 and erbB4 (Lee et al., *Nature* 378:394–398 (1995); Gassmann, et al., *Nature* 378:390–394 (1995)), but rather on endocardial cells. Expression of any of the other receptors for Ephrin B family ligands (Eph B1, B2, B3 and A4) was detected in this tissue. This suggests that in the heart, ligand-receptor interactions among endothelial cells may in turn affect interactions with smooth muscle cells.

Example 8

Ephrin B2 is Required for Vascularization of the Neural Tube

In EphrinB2$^{tlacZ}$/EphrinB2$^{tlacZ}$ embryos, capillary ingrowth into the neural tube failed to occur. Instead, EphrinB2-expressing endothelial cells remained associated with the exterior surface of the developing spinal cord. Comparison of β-galactosidase expression with pan-endothelial PECAM-1 and EphB4 expression provided no evidence of a separate, venous capillary network expressing EphB4 in the CNS at this early stage (E9–E10). Rather, expression of a different EphrinB2 receptor, EphB2, was seen in the neural tube as previously reported (Henkemeyer, et al., *Oncogene* 9:1001–1014 (1994)), where no gross morphological or patterning defects were detectable. In this case, therefore, the mutation does not appear to cause a non-autonomous phenotype in receptor-expressing cells, rather only an autonomous effect on ligand-expressing cells.

Example 9

EphrinB2 is Artery-specific in Adult Tissues

To determine whether ephrin-B2 is expressed in adult tissues in an artery-specific manner, we performed histochemical staining for β-galactosidase on ephrin-B2$^{tlacZ}$/+ heterozygous mice. Antibody staining for PECAM-1, a pan-endothelial marker, was performed on the same or on adjacent sections to reveal non-arterial vessels (i.e., veins). Ephrin-B2 is expressed throughout the adult mouse in an artery-specific manner, in tissues including the heart, leg muscle, kidney, liver and fat. Expression was detected in vessels of all diameters, including large arteries, arterioles and the smallest-diameter capillaries. It had been previously assumed that capillaries by definition have neither arterial nor venous identity. These results show that this is not the case, and that arterial identity extends into the capillary beds.

Sections through adult arteries were double labeled by histochemical staining for β-galactosidase (lacZ) to reveal ephrin-B2-taulacZ expression, and with antibody to PECAM-1 as a pan-endothelial marker. LacZ (blue from X-gal) staining revealed ephrinB2 expression in the dorsal aorta but not in the inferior vena cava, in the femoral artery next to the leg bone, but not in the femoral vein, and in the coronary epicardial artery, but not in the coronary vein.

Similar staining of other sections revealed the presence of EphrinB2 in kidney arteriole, liver arteriole and small muscle arteriole, as well as arterial capillary. Kidney venule, hepatic vein, and muscle veins were lacZ-negative but PECAM-1 positive.

Gut fat was stained for lacZ (β-galactosidase) and labeled with PECAM-1 to reveal venous vessels as well as arterial vessels. EphrinB2 is expressed by arterioles and arterial capillaries but not in PECAM-1 positive venule. A further section showed that EphrinB2 is expressed by arterial capillaries surrounded by PECAM-1 positive non-arterial capillaries.

Example 10

Ephrin-B2 is Expressed During Tumor Angiogenesis

It had been assumed that tumor vessels sprout from the post-capillary venules. To address the question of whether EphrinB2 is expressed during tumor angiogenesis, Lewis Lung Carcinomas were implanted subcutaneously in the dorsal region of ephrin-B2$^{taulacZ}$/+ heterozygous females. After one week, the tumors were removed and processed for β-galactosidase histochemistry in whole mounts. The results indicate clearly that ephrin-B2 is in fact expressed by tumor vessels. This was confirmed by double-staining of sections cut through such tumors, for β-galactosidase and PECAM-1.

EphrinB2 Expression by Tumor Capillaries

Lewis Lung Carcinoma (LLC) cells were implanted subcutaneously in the dorsal region of EphrinB2-taulacZ heterozygous females. After one week, tumors were removed for staining. EphrinB2 positive arterial capillaries were observed in peripheral tumor tissue. Double labeling using anti-PECAM-1 antibodies and X-Gal revealed colocalization of the EphrinB2 lacZ (staining blue) and PECAM-1 (staining brown) signals in arterial capillaries, but that non-arterial capillaries were labeled by anti-PECAM-1 antibody only.

Example 11

Screen for Clones Containing Artery-specific Genes

A summary of the screening procedures used to identify clones containing artery-specific genes is provided in Appendix I. Briefly, endothelial cells were isolated from dissociated embryonic yolk sac, vitelline arteries or vitelline veins using positive selection with antibody to PECAM-1 (magnetic beads with antibody or FACS). cDNA was synthesized from lysates of either single cells or small numbers (ca. 200) of cells, and amplified by PCR. To confirm that the cDNAs were from arterial or venous endothelial cells, the cDNA synthesized from each cell preparation was Southern blotted and hybridized in quadruplicate with a series of probes, including tubulin (ubiquitously expressed), the pan-endothelial probes Flk1 and Flt1, and the arterial-specific probe ephrin-B2. Cell preparations containing cDNAs that were positive for Flk1, Flt1 and ephrin-B2 probes were considered arterial, while those that were positive for the pan-endothelial markers (Flk1 and Flt1) but not ephrin-B2 were considered venous. Thus, the use of ephrin-B2 probes in this procedure was essential to confirm the arterial and/or venous nature of the synthesized cDNAs.

To isolate additional arterial-specific genes from these cDNAs, they were cloned into a phage lambda vector to generate cDNA libraries. Plaques from these libraries were then screened using duplicate filter lifts with arterial- or venous-specific cDNA probes made from either single cells or pools of cells. Plaques exhibiting differential hybridization to the arterial probes, as compared to the venous probes, were isolated, and the inserts were amplified using T3 and T7 primers, and re-analyzed by cDNA Southern blotting. Two different pairs of arterial-venous endothelial cells (vitelline artery and vein cells, and single yolk sac arterial and venous endothelial cells) were used in the Southern blot. Most of the clones were strongly expressed in arterial cells, and expressed weakly or not detectably by venous cells. The initial screen was designed to isolate additional arterial-specific genes. Twelve candidate arterial-specific clones were isolated using the single-cell probes, while one clone was isolated using the pooled probes. In vivo arterial-specific expression of these genes can be confirmed by in situ hybridization experiments. Methods such as these can be applied to arterial-specific cells (e.g., arterial endothelial cells, arterial smooth muscle cells) or venous-specific cells (venous endothelial cells, venous smooth muscle cells).

These data show that it will be possible to isolate novel arterial- or venous-specific genes from single cells (e.g., endothelial cells, smooth muscle cells). Such vessel type-restricted genes may provide insights into the physiological differences between arterial and venous cells (e.g., endothelial cells, smooth muscle cells). Methods such as those described herein can also identify genes involved in the etiology of arterial- and/or venous-specific diseases, such as arterial hypertension, atherosclerosis, deep venous thrombosis, and certain types of venous malformations. In addition, the methods can be used to detect candidate genes which are involved in human genetic disorders of the circulatory system. Such identified genes and/or gene products can then serve as novel drug targets.

Appendix I: Single Cell PCR, 3' cDNA Library Construction and Differential Screening Procedure to Isolate Novel Arterial- or Venous-Specific Genes 1. Dissection of vitelline arteries and vitelline veins from E12.5 to E14.5 yolk sacs, based on morphological criteria.
2. Dissociation of yolk sacs in collagenase solution (5 mg/ml) at 37° C. for 45'.
3. Isolate single or small groups of endothelial cells (ECs) by one of the following methods.
   a) Magnetic bead-based separation using PECAM-1 as primary antibody.
   b) FACS purification using PECAM-1-FITC primary antibody.

c) GFP fluorescence from tie2-GFP transgenic mouse for endothelial cell identification, followed by microcapillary mouth-pipeting.
4. Lyse the single cells in PCR tubes at 65° C. for 1'.
5. Keep 1–2' at room temperature to allow the oligo-T to anneal to RNA.
6. Reverse transcription using AMV and MMLV enzyme mixture, at 37° C. for 15'.
7. Poly-A tailing with terminal transferase and dATP, at 37° C. for 15'.
8. PCR reaction set up:
   100 µl reaction, 5-fold normal level of dNTP mix, high concentration of Taq.
   Using a single PCR primer with 24 (T)s at 3' end for symmetrical amplification.
9. cDNA Southern blotting with endothelial specific and arterial/venous specific 3' probes on the amplified cDNAs for each cell prep.
10. Select a few good cells that give strong signals for the appropriate probes. Isolate cDNAs from 500 bp to 2 kb on agarose gel.
11. Precipitate and quantify cDNA.
12. Ligate into lambda ZAPII (Stratagene; LaJolla, Calif.) phage arms for cDNA libraries.
13. Plate the library at very low density: 1000 pfu/plate. Take duplicate filter lifts.
14. Screen duplicate filters with probes made from vitelline artery cells and vitelline vein cells.
15. Pick differentially expressed phage clones. Confirm differential expression of phage clones by performing reverse (cDNA) Southern blotting of phage inserts using probes made from vitelline artery cells and vitelline vein cells.
16. In situ hybridization to examine the expression patterns of cDNA fragments.

Example 12

Generation of Monoclonal Antibodies against the Extracellular Domain of Ephrin-B2

While polyclonal rabbit antibodies to fragments of ephrin-B2 expressed in bacteria had previously been reported, such antibodies are typically not reactive with native forms of the protein on the cell surface, and therefore are not useful for many applications (e.g., cell sorting, functional inhibition, drug-targeting). To generate antibodies with more desirable binding properties, we expressed the extracellular domain of ephrin-B2 as a glycophosphatidylinositol (GPI)-linked form on Chinese Hamster Ovary (CHO) cells. Hamsters were immunized with these cells, hybridomas were prepared by fusion with mouse myeloma cells, and supernatants were screened using COS cells which expressed ephrin-B2-GPI.

Supernatant from clone #6E3 bound well to ephrinB2 on live COS cells. The ephrin-B2-GPI COS cell lines are a pooled population of G418-selected cells, with 30% of the cells being positive for ephrinB2. Control (untransfected) COS cells were negative when stained with the same antibody.

Example 13

Some anti-ephrin-B2 Antibodies Block the EphB2-ephrinB2 Binding Interaction

In cases where the antibodies also block function (i.e., inhibit binding of ephrin-B2 to its receptors), they can be used as potential anti-angiogenic agents. To identify such function-inhibiting antibodies, we screened 12 hamster anti-EphrinB2 hybridoma supernatants for their ability to reduce the binding of GPI-ephrin-B2 (expressed on COS cells) to a soluble EphB2-Fc fusion protein. Binding was detected by $^{125}$I-labeled goat anti-human Fc antibody. Pre-incubation of cells with various supernatants revealed that the majority of the antibodies have no blocking effects on subsequent receptor-ligand binding (control as 100%), even though these supernatants all contained antibodies that bound to ephrin-B2-GPI. One of the antibodies (5E11) produced a 40% reduction in EphB2-Fc binding to the ephrin-B2-GPI COS cells.

Additional Studies Addressing Expression of EphrinB2

The vertebrate circulatory system is comprised of arteries and veins, defined by the direction of blood flow. Although arteries and veins differ in their structure, for the last century it had been assumed that these distinctions reflected the influence of physiological factors such as hemodynamic forces, blood pressure, pH and oxygenation levels, rather than any intrinsic difference between the cells comprising these vessel types. As described herein, arterial and venous endothelial cells (ECs) are genetically distinct, from the earliest stages of angiogenesis (see also, Wang, H. U., et al., *Cell* 93:741–753 (1998)). This genetic difference is represented not simply by anonymous molecular markers, but rather by complementary expression of an interacting cell surface ligand-receptor pair: ephrinB2, a transmembrane ligand is expressed by arteries, whereas one of its receptors, the tyrosine kinase EphB4, is expressed on veins (Bergemann, A. D., et al, *Oncogene* 16:471–480 (1995); Wang, H. U., et al., *Cell* 93:741–753 (1998); Bennett, B. D., et al., *Proc. Natl. Acad. Sci. USA* 92:1866–1870 (1995)). Other genes expressed by arteries but not expressed by veins have subsequently been identified as well (see, e.g., Bianchi C., et al. *Exp. Cell Res.* 248:329–338 (1999); Roose, J. et al., *Nucleic Acid Res.* 26:469–476 (1998); Tian, H. et al., *Genes Dev.* 12:3320–3324 (1998)).

EphrinB2 and EphB4 are not simply markers of arterial and venous endothelial cells; as described herein, their function is essential for proper development of the cardiovascular system. Targeted null mutations in ephrinB2 cause embryonic lethality by E10.0, accompanied by defects in angiogenic remodeling of the peripheral vasculature and defective myocardial trabeculation in the heart (Adams, R. et al., *Genes Dev.* 13:295–306 (1999); Wang, H. U., et al., *Cell* 93:741–753 (1998). Moreover, it has been demonstrated that EphB4−/− mutants exhibit an almost identical phenotype (Gerety, S. S., et al., *Mol. Cell* 4:403–414 (1999)). As EphB4 is known to interact only with ephrinB2 among all ephrinB-class ligands (Bergemann, A. D., et al., *Oncogene* 16:471–480 (1998); Brambilla, R., et al., *Mol. Cell Neurosci.* 8:199–209 (1996); Brambilla, R., et al., *EMBO J.* 14:3116–3126 (1995); Sakano, S. et al., *Oncogene* 13:813–822 (1996)), these data suggest that ligand-receptor interactions between ephrinB2 and EphB4 are essential for cardiovascular development. Furthermore, since ephrinB-class transmembrane ligands are capable of signal transduction upon engagement of EphB-class receptors (Bruckner, K., et al., *Science* 275:1640–1643 (1997); Holland, S. J., et al., *Nature* 383:722–725 (1996)), the symmetrical phenotypes of ephrinB2 and EphB4 mutants suggest that this ligand-receptor pair mediates bi-directional signaling between the tissues that express them.

An important question raised by these studies is whether the arterial-specific expression of ephrinB2 persists into adulthood, in either stable and/or newly forming blood vessels. This question is important for two reasons. First, it was not clear whether the identity distinctions between arteries and veins required to assemble the circulatory system necessarily need to be maintained once development is complete. Indeed, at least one other artery-specific gene, EVEC/DANCE, is strongly down-regulated in adult vessels and is only re-expressed at sites of injury (Kowal, R. C., et al, Circ. Res. 84:1166–1176 (1999); Nakamura, T., et al., J. Biol. Chem. 274:22476–22483 (1999)). Second, the essential requirement of ephrinB2 for embryonic angiogenesis raised the possibility that it might be functionally important in settings of adult angiogenesis as well, like other signaling molecules involved in blood vessel development (Lin, P., et al., Proc. Natl. Acad. Sci. USA 95:8829–8834 (1998)). Thus, Examples 14–16 address the questions of whether ephrinB2 is expressed in adults, at sites of adult neovascularization, and whether ephrinB2 is expressed in a subset of blood vessels.

Example 14

Expression of EphrinB2 in Adult Arteries, Microvessels and Capillaries

Experimental Procedures

Histochemical and Immunocytochemical Analysis

Animals were anesthetized and perfused with 0.1M PIPES (pH 7.0) followed by 2% paraformaldehyde (PFA)/0.1 M PIPES at a constant pressure of ~80 mm Hg. Vessel segments were excised and placed in 0.2% PFA/PIPES overnight at 4° C., rinsed and stained for 3.5 hours in X-Gal buffer (1.6 mg/ml potassium ferricyanide, 2.2 mg/ml potassium ferrocyanide, 0.2 mg/ml $MgCl_2$, 0.1 mg/ml sodium deoxycholate, 0.02% NP-40, 1 mg/ml X-Gal in 0.1M PIPES (pH 7.0)). LacZ-stained vessels were embedded in OCT and sectioned at 10 µm. Sections were then air-dried and post-fixed in 2% PFA/PBS. Organs were excised, embedded in OCT and sectioned at 20 µm. Sections were stained in X-Gal buffer for 6 hours to overnight at 30° C. and postfixed in 2% PFA/PBS for 5 minutes.

For X-Gal staining of cutaneous wound and corneal tissues, samples were immersion fixed from 1 to 4 hours in 2–4% paraformaldehyde, incubated overnight in 30% sucrose in phosphate-buffered saline (PBS) at 4° C. and stained for 1 to 6 hours at 37° C. in X-Gal buffer as described (Gerety, S. S., et al., Mol. Cell 4:403–414 (1999); Wang, H. U., et al., Cell 93:741–753 (1998)). Immunohistochemical analysis was performed on cryostat sections and X-Gal stained sections. Primary antibodies were the following: anti-mouse PECAM-1 (clone MEC 13.3, Pharmingen, San Diego, Calif.), anti-β gal (5-prime, 3-prime), anti-BrdU (Accurate), and Cy3-conjugated anti-SMA (Sigma, St. Louis, Mo.). HRP-conjugated anti-rat secondary antibody (Jackson Immuno Research Laboratories, Bar Harbor, Me.) was used for PECAM-1 staining on X-Gal stained sections. For fluorescence staining, the following secondary antibodies were used: Alexsa 488-conjugated anti-rabbit I-G (Molecular Probes Inc, Eugene, Oreg.) or Cy5-conjugated anti-rabbit IgG (Jackson Immuno Research Laboratories, Bar Harbor, Me.) and Cy3-conjugated anti-rat IgG (Jackson Immuno Research Laboratories, Bar Harbor, Me.).

Results

To examine the expression of ephrinB2 in adult mice, we exploited the fact that the targeted ephrinB2 knockout allele that we had previously generated contains a taulacZ reporter gene (Lundgren, S. E., et al., Development 121:1769–1773 (1995); Mombaerts, P., et al., Cell 87:675–686 (1996)) fused in-frame with the ephrinB2 initiator codon (Wang, H. U., et al., Cell 93:741–753 (1998)). This reporter provides a convenient histochemical indicator of ephrinB2 transcription, that is more sensitive than in situ hybridization. A comparison of ephrinB2$^{taulacZ}$ expression with that of authentic ephrinB2 mRNA previously indicated that the taulacZ reporter faithfully reproduces the expression pattern of the endogenous gene in embryos (Bergemann, A. D., et al., Oncogene 16:471–480 (1995); Sakano, S., et al., Oncogene 13:813–822 (1996); Wang, H. U., and Anderson, D. J., Neuron 18:383–396 (1997); Wang, H. U., et al., Cell 93:741–753 (1998)). Similar ephrinB2 reporter mice have been independently generated by others and show essentially the same expression pattern (Adams, R., et al., Genes Dev. 13: 295–306 (1999); Gale, N. W., et al., Dev. Biol. 230:151–160 (2001)). As our ephrin $B2^{taulacZ/+}$ heterozygous "indicator" mice are viable and fertile, we could examine the expression of the taulacZ marker gene in adult animals of this genotype, to reveal sites of ephrinB2 gene expression in the vasculature.

Sections through various adult organs of ephrin $B2^{taulacZ/+}$ mice revealed expression in arteries of varied diameters (see, e.g, U.S. Provisional Application No. 60/252,009, filed on Nov. 20, 2000, FIG. 1, arrowheads). These tissues included the kidney (see, e.g, U.S. Provisional Application No. 60/252,009, filed on Nov. 20, 2000, FIG. 1A), heart (see, e.g, U.S. Provisional Application No. 60/252,009, filed on Nov. 20, 2000, FIG. 1B), liver (see, e.g, U.S. Provisional Application No. 60/252,009, filed on Nov. 20, 2000, FIG. 1C, E), spleen (see, e.g, U.S. Provisional Application No. 60/252,009, filed on Nov. 20, 2000, FIG. 1D), fat (see, e.g, U.S. Provisional Application No. 60/252,009, filed on Nov. 20, 2000, FIG. 1F), muscle (see, e.g, U.S. Provisional Application No. 60/252,009, filed on Nov. 20, 2000, FIG. 1G) and brain (see, e.g, U.S. Provisional Application No. 60/252,009, filed on Nov. 20, 2000, FIG. 1H). Although in most sections there was little or no detectable venous staining (see, e.g, U.S. Provisional Application No. 60/252,009, filed on Nov. 20, 2000, FIG. 1, arrows), in some sections, there appeared to be a patchy, low-level expression of the reporter in veins. To examine this more clearly, we stained the dorsal aorta and vena cava of indicator mice in whole mount, and opened the vessels to visualize the luminal surface enface (see, e.g, U.S. Provisional Application No. 60/252,009, filed on Nov. 20, 2000, FIG. 2). With X-Gal reaction times (3 hours) that completely saturated the staining in the dorsal aorta (see, e.g, U.S. Provisional Application No. 60/252,009, filed on Nov. 20, 2000, FIG. 2A), patchy staining was visible in the vena cava (see, e.g, U.S. Provisional Application No. 60/252,009, filed on Nov. 20, 2000, FIG. 2B). This staining had two characteristic morphologies: narrow longitudinal stripes (see, e.g, U.S. Provisional Application No. 60/252,009, filed on Nov. 20, 2000, FIG. 2B, arrow), and smaller patches (see, e.g, U.S. Provisional Application No. 60/252,009, filed on Nov. 20, 2000, FIG. 2B, arrowhead). Double-label confocal immunofluorescence microscopy with antibodies to β-galactosidase (see, e.g, U.S. Provisional Application No. 60/252,009, filed on Nov. 20, 2000, FIG. 2D, red) and the pan-endothelial marker PECAM-1 (see, e.g, U.S. Provisional Application No. 60/252,009, filed on Nov. 20, 2000, FIG. 2D, green) revealed that the patches of weak β-galactosidase expression occurred in endothelial cells (see, e.g, U.S. Provisional Application No. 60/252,009, filed on Nov. 20, 2000, FIG. 2D, arrowheads), while the longitudinal stripes did not (see, e.g, U.S. Provisional Application No. 60/252,009, filed on Nov. 20, 2000, FIG. 2D, arrows). It is possible that these longitudinal stripes represent the vaso vasorum, the small vessels of arterial origin that supply blood to the walls of large veins. Interestingly, the en face visualization revealed a characteristic wavy pattern of endothelial cells in the aorta (see, e.g, U.S. Provisional Application No. 60/252,009, filed on Nov. 20, 2000, FIG. 2C, 2G) that was not seen in the vena cava (see, e.g, U.S. Provisional Application No. 60/252,009, filed on Nov. 20, 2000, FIG. 2D, 2H). This difference in the distortion of the intimal surface may reflect differences in the ambient conditions of the two vessel types at the time of fixation.

The recent availability of EphB4$^{taulacZ/+}$ indicator mice (Gerety, S. S., et al., Mol. Cell 4:403–414 (1999)) permitted us to determine whether the preferential expression of EphB4 in veins persists into adulthood as well. Expression of EphB4 was clearly detected in adult veins such as the vena cava (see, e.g, U.S. Provisional Application No. 60/252,009, filed on Nov. 20, 2000, FIG. 2F). However, EphB4 expression in the vena cava was not uniform, but rather distributed in islands of contiguous endothelial cells (see, e.g, U.S. Provisional Application No. 60/252,009, filed on Nov. 20, 2000, FIG. 2F, 2H, 2J), revealing an apparent cellular heterogeneity in the composition of the venous endothelial wall. Individual EphB4$^+$ cells could also be detected in the dorsal aorta (see, e.g, U.S. Provisional Application No. 60/252,009, filed on Nov. 20, 2000, FIG. 2E, arrow), as well as in other arteries. The level of EphB4 expression in these scattered arterial endothelial cells was clearly lower than that in veins, however, when revealed by anti-β-galactosidase antibody staining rather than by the non-linear X-Gal histochemical reaction (see, e.g, U.S. Provisional Application No. 60/252,009, filed on Nov. 20, 2000, FIG. 2G vs. 2H, 2I vs. 2J). The EphB4$^+$ cells in the endothelial layer of the aorta were found primarily in the narrow "peaks" of the waves in the endothelial sheet (see, e.g, U.S. Provisional Application No. 60/252,009, filed on Nov. 20, 2000, FIG. 2E, arrow, narrow lines and FIG. 2I, arrow), but some could also be seen in the broader "troughs" (see, e.g, U.S. Provisional Application No. 60/252,009, filed on Nov. 20, 2000, FIG. 2E, arrowhead).

Expression of ephrinB2 in the adult vasculature was evident not only in major vessels, but persisted into the smallest-diameter microvessels and capillaries. Double-labeling with antibody to PECAM-1 revealed that ephrinB2 was expressed in a subset of these microvessels (see, e.g, U.S. Provisional Application No. 60/252,009, filed on Nov. 20, 2000, FIG. 3). This was evident in multiple tissues, including pancreas (see, e.g, U.S. Provisional Application No. 60/252,009, filed on Nov. 20, 2000, FIG. 3A), muscle (see, e.g, U.S. Provisional Application No. 60/252,009, filed on Nov. 20, 2000, FIG. 3B, 3J–3L), intestinal fat (see, e.g, U.S. Provisional Application No. 60/252,009, filed on Nov. 20, 2000, FIG. 3C), kidney glomeruli (see, e.g, U.S. Provisional Application No. 60/252,009, filed on Nov. 20, 2000, FIG. 3D–3F), and brain, liver, adrenal cortex and adrenal medulla. Similarly, expression of EphB4$^{taulacZ}$ extended from larger-diameter veins into a subset of microvessels and capillaries in the glomerulus of the kidney (see, e.g, U.S. Provisional Application No. 60/252,009, filed on Nov. 20, 2000, FIG. 3G–3I) and muscle (see, e.g, U.S. Provisional Application No. 60/252,009, filed on Nov. 20, 2000, FIG. 3M–3O). Thus, it is clear that expression of ephrinB2 persists in adult arteries, and extends into some of the smallest microvessels.

Discussion (Molecular Distinctions Between Arteries and Veins Persist Into Adulthood)

EphrinB2 is the first gene to be described that is expressed in an arterial-specific manner from early in embryogenesis into adulthood, and which is functionally essential for angiogenesis as well. Recently, the transmembrane receptor protein tyrosine phosphatase μ (RPTPμ) has been shown to be expressed in adult arteries but not veins, in a variety of tissues (Bianchi, C., et al., Exp. Cell Res. 248:329–338 (1999)). However, in contrast to ephrinB2, RPTPμ is expressed in an apparently pan-endothelial manner in the embryo (Fuchs, M., et al., Mech Dev. 70:91–109 (1998); Sommer, L., et al., Dev. Dyn. 208:48–61 (1996)). Furthermore, no functional role for RPTPμ in angiogenesis has yet been demonstrated.

In addition to transmembrane proteins such as ephrinB2 and RPTPμ, several transcription factors have been reported to be specifically expressed in arterial endothelial cells. Sox-13, an HMG box factor, is expressed in embryonic arteries but not veins of mid-gestational embryos (Roose, J., et al., Nucleic Acid Res. 26:469–476 (1998)). However, unlike ephrinB2, which is expressed in developing blood vessels as early as E8–E8.5, expression of Sox-13 is not detected until E13.5. It is not yet clear whether the artery-specific expression of Sox-13 is maintained into adulthood, nor is it clear whether this gene is functionally important for angiogenesis. EPAS-1, a close relative of the hypoxia-inducible factor 1α transcription factor (Ema, M., et al., Proc. Natl. Acad. Sci. USA 94:4273–4278 (1997); Flamme, I., et al., Mech. Dev. 63:51–60 (1997); Tian, H., et al., Genes Dev. 11:72–82 (1997)), has been reported to be expressed in developing arteries but not veins where it is detected as early as E11.5 (Tian, H., et al., Genes Dev. 12:3320–3324 (1998)). Other studies, however, have reported low-level expression of the gene in the cardinal veins (Flamme, I., et al., Mech Dev. 63:51–60 (1997)). Whether vessel-specific expression of EPAS-1 persists into adulthood is not yet known. A knockout in EPAS-1 causes mid-gestational embryonic lethality (Tian, H., et al., Genes Dev. 12:3320–3324 (1998)), and recent data suggest that the gene is required for vascular remodeling (Peng, J., et al., Proc. Natl. Acad. Sci. USA 97:8386–8391 (2000)). Members of a novel family of Hairy-related bHLH transcription factors, HRT1-3, have also been shown recently to be expressed specifically in arterial cells during embryonic development, but whether this arterial specificity persists into adulthood is not yet clear (Nakagawa, O., et al., Dev. Biol. 216:72–84 (1999)). Interestingly, these genes appear closely related to the zebrafish gene gridlock, which is expressed early in arterial development and is required for proper aorta assembly (Zhong, T. P., et al., Science 287:1820–1824 (2000)).

An interesting finding was the apparent heterogeneity of EphB4 expression in the endothelial layer of the vena cava (see, e.g, U.S. Provisional Application No. 60/252,009, filed on Nov. 20, 2000, FIG. 2F and 2H). The existence of EphB4$^-$ cells in the vein could reflect either stochastic inactivation of gene expression in a subset of cells during development, or the intercalation of non-expressing endothelial cells from circulating precursors (Asahara, T., et al., Science 275:964–967 (1997)). We cannot exclude that this heterogeneity is characteristic of the reporter but not of the endogenous gene, for example, due to mosaic inactivation of the targeted locus; the low signal and high background obtained with EphB4 in situ hybridization probes precludes a direct comparison of EphB4 mRNA and lacZ expression in this tissue. However, the fact that groups of EphB4$^+$ and EphB4$^-$ cells segregate from one another in the venous endothelium suggests that the lacZ$^+$ and lacZ$^-$ cells differ in ways more fundamental than simply reporter gene expression. The lineage relationship of the cells within the lacZ$^+$ patches is not clear; they could be clonally related, or reflect selective adhesion of non-clonally related EphB4$^+$ endothelial cells. Whatever the case, the observation of such segregation is consistent with the idea that EphB4 signaling plays a role in the maintenance of boundaries between expressing and non-expressing cells (Mellitzer, G., et al, *Nature* 400:77–81 (1999); Xu, Q., et al., *Nature* 399:267–271 (1999)). Whether the patches of EphB4$^-$ venous endothelial cells correspond, conversely, to the patches of ephrinB2$^+$ cells found in the veins (see, e.g, U.S. Provisional Application No. 60/252,009, filed on Nov. 20, 2000, FIG. 2B and 2D, arrowheads) is not yet clear, because the appropriate reagents are not yet available to perform double-labeling for both ligand and receptor.

It is particularly striking that expression of ephrinB2 and EphB4 in the adult vasculature extends into the smallest-diameter microvessels and capillaries in a variety of tissues. This observation suggests that capillaries, as well as larger-diameter vessels, can have arterial and venous identity. Previous support for this idea derived from enzymatic histochemical staining of the capillary beds: the arterial side of the capillary bed expresses alkaline phosphatase, while the venous side expresses dipeptidylpeptidase IV (DPPIV) (Koyama, T., et al., *Jap. J. Physiol* 48:229–241 (1998); Lojda, Z. *Histochemistry* 59:153–166 (1979); Mrázková, O., et al., *Am. J. Anat.* 177:141–148 (1986)). Whether these enzymatic differences reflect differences in gene expression, or differences in activity due to post-transcriptional or post-translational mechanisms, is not clear. The nature of the transition between the arterial and venous domains of the capillary bed also remains uncertain. The abovementioned histochemical staining technique demonstrated a "transitional zone" in which both the arterial and venous activities overlap (Mrázková, O., et al., *Am. J. Anat.* 177:141–148 (1986)), but whether this reflects co-expression of both activities in individual endothelial cells or a zone of intermixing between cells expressing one or the other marker remains to be determined. Double-labeling for ephrinB2 and EphB4 may help to resolve this issue, once the appropriate reagents are available.

Example 15

Expression of EphrinB2 in Arterial Smooth Muscle Cells

Experimental Procedures

Histochemical and Immunocytochemical Analysis was Performed as Described in Example 13.

Results

In the course of examining the expression of the ephrinB2$^{tau lacZ}$ indicator gene in arteries we noticed that expression of the marker appeared to extend from the endothelial into the smooth muscle layer (see, e.g., U.S. Provisional Application No. 60/252,009, filed on Nov. 20, 2000, FIG. 4A–4D). Such smooth muscle expression of ephrinB2 was not detected in the veins examined in this study (see, e.g, U.S. Provisional Application No. 60/252,009, filed on Nov. 20, 2000, FIG. 4D, VC). Double-labeling with antibodies to β-galactosidase (see, e.g, U.S. Provisional Application No. 60/252,009, filed on Nov. 20, 2000, FIG. 4F, red) and alpha smooth muscle actin (SMA) (see, e.g, U.S. Provisional Application No. 60/252,009, filed on Nov. 20, 2000, FIG. 4F, green) confirmed that ephrinB2 is expressed in smooth muscle cells in the arterial walls (see, e.g, U.S. Provisional Application No. 60/252,009, filed on Nov. 20, 2000, FIG. 4F, yellow patches), although not all of the smooth muscle cells were ephrinB2$^+$. Because of the close apposition of endothelial and smooth muscle cells in these adult vessels and diffusion of the X-Gal reaction product, it was difficult to determine whether ephrinB2 expression was in fact maintained in arterial endothelial cells (see, e.g., U.S. Provisional Application No. 60/252,009, filed on Nov. 20, 2000, FIG. 4A–4D, arrows). This was confirmed, however, by double-label immunofluorescence with antibodies to β-galactosidase and PECAM-1 (see, e.g, U.S. Provisional Application No. 60/252,009, filed on Nov. 20, 2000, FIG. 4E, yellow staining).

The observation of ephrinB2 expression in adult arterial smooth muscle cells was surprising, as initial studies of its expression in embryonic arteries had failed to detect it in the smooth muscle layer (Adams, R., et al., *Genes Dev.* 13: 295–306 (1999); Wang, H. U., et al., *Cell* 93:741–753 (1998)). However, these studies were performed in very early embryos (E9.5–E10.5), raising the possibility that ephrinB2 became expressed in arterial smooth muscle cells at later stages of development not previously examined. In confirmation of this idea, double-label immunofluorescence staining with antibodies to β-galactosidase and alpha SMA revealed that ephrinB2 was not expressed in the smooth muscle layer of the dorsal aorta even at E11.5 (see, e.g, U.S. Provisional Application No. 60/252,009, filed on Nov. 20, 2000, FIG. 5A–5C), but first became detectable in this region at E12.5 (see, e.g., U.S. Provisional Application No. 60/252,009, filed on Nov. 20, 2000, FIG. 5D–5F), four to five days after its expression in arterial endothelial cells can first be detected (Wang, H. U., et al., *Cell* 93:741–753 (1998)). Strikingly, the initial expression of ephrinB2 in arterial smooth muscle cells occurred in those alpha SMA$^+$ cells closest to the endothelial layer (see, e.g, U.S. Provisional Application No. 60/252,009, filed on Nov. 20, 2000, FIG. 5F, yellow staining). By E13.5, expression of ephrinB2 had extended more deeply into the smooth muscle layer (see, e.g, U.S. Provisional Application No. 60/252,009, filed on Nov. 20, 2000, FIG. 5G). At these embryonic stages, expression of ephrinB2 in the endothelial layer was stronger than in the smooth muscle layer. However, in adults, the levels of expression in the two layers were comparable (see, e.g, U.S. Provisional Application No. 60/252,009, filed on Nov. 20, 2000, FIG. 5J and FIG. 4E).

Discussion (EphrinB2 is Expressed Preferentially in Arterial Vascular Smooth Muscle)

Another unexpected finding in the course of these studies was that ephrinB2 is expressed not only in arterial endothelial cells, but also in smooth muscle cells of arteries but not veins. This observation indicates that arterial smooth muscle cells are also molecularly distinct from their venous counterparts. The only other documented examples of such arterial-specific smooth muscle gene expression are EVEC/DANCE, an EGF-like-repeat-containing secreted protein (Kowal, R. C., et al, *Circ. Res.* 84:1166–1176 (1999); Nakamura, T., et al., *J. Biol. Chem.* 274:22476–22483 (1999)), and the 'latent TGFβ-binding protein-2' (LTBP-2) (Fang, J., et al., *Biochim. Biophys. Acta* 1354:219–230 (1997)). Unlike ephrinB2, however, expression of EVEC/DANCE is down-regulated after development and is virtually undetectable in adult arterial smooth muscle, although it can be re-induced upon injury (Kowal, R. C., et al., *Circ. Res.* 84:1166–1176 (1999); Nakamura, T., et al., *J. Biol. Chem.* 274:22476–22483 (1999)). LTBP-2 expression has only been examined in mid- to late-gestational embryos (Fang, J., et al., *Biochim. Biophys. Acta* 1354:219–230 (1997)), so it is not clear whether its expression persists into adulthood, and if so whether its artery specificity is maintained. To our knowledge, therefore, ephrinB2 is the first example of a gene that is expressed preferentially in arterial compared to venous vascular smooth muscle from early embryogenesis through adulthood. The existence of persistent differences in gene expression between arterial and venous smooth muscle cells may underlie the fundamental differences observed in the organizational architecture of arteries and veins of comparable internal diameters. Interestingly, the observation that promoter elements of the smooth muscle-specific SM22 gene direct expression in arterial but not venous smooth muscle cells in transgenic mice (Li, L., et al., *J. Cell Biol.* 132:849–859 (1996)) provides evidence that even genes which are expressed in all vascular smooth muscle cells may be controlled by distinct transcriptional regulatory programs in arteries and veins.

The expression of ephrinB2 in arterial vascular smooth muscle was missed in initial studies of ephrinB2 expression in the cardiovascular system (Adams, R., et al., *Genes Dev.* 13:295–306 (1999); Wang, H. U., et al., *Cell* 93:741–753 (1998)), because the analysis was restricted to embryonic stages before E10.5, and the gene is not activated in smooth muscle until E12.5. This observation suggests that distinct mechanisms may control the timing of onset of ephrinB2 expression in endothelial cells and vascular smooth muscle cells. Interestingly, the first detectable expression of ephrinB2 in vascular smooth muscle cells (VSMCs) was in the layer immediately adjacent to the endothelium. This observation suggests that an inductive signal from arterial endothelial cells (ECs) to VSMCs may induce expression of ephrinB2 in the latter cells.

Example 16

Expression of EphrinB2 in Subsets of Microvessels at Sites of Neovascularization and Additional Tumor Angiogenesis Studies Experimental Procedures Comeal Micropocket Assay Corneal pockets were made in murine corneas as described (Kenyon, B. M., et al., *Invest. Opthamol. Vis. Sci.* 37:1625–32 (1996)). A 0.34×0.34 mm sucrose aluminum sulfate (Bukh Meditec) pellet coated with hydron polymer type NCC (IFN Science) containing 200 ng of VEGF was implanted into the corneal pocket. Pellets were positioned at 1.0 mm from the corneal limbus, and erythromycin ophthalamic ointment (E. Foufera) was applied to each operated eye. The corneas of all mice were examined by slit-lamp biomicroscopy on postoperative day 3 and 5 after pellet implantation. At day 5, corneas were collected for LacZ staining and immunohistochemistry.

5'-Bromo-2'-Deoxyuridine (BrdU) Labeling

An osmotic pump (Alzet, Cupertino, Calif.) containing 4.4 mg of BrdU (Sigma, St. Louis, Mo.) was implanted subcutaneously at a lateral position in the neck of mice immediately after they had received corneal micropocket surgery. The pump was prepared to deliver 26 gg of BrdU per hour for 7 days.

Wound Healing Model

The skin of an ephrinB2$^{taulacZ/+}$ heterozygous mouse was cleansed with 70% alcohol, and a full-thickness wound was made using a sterile, disposable 4 mm punch biopsy (Baker Cummins Dermatological). Skin tissues with and without a wound were harvested for histological examination at day 7 following wounding.

Tumor Models

Lewis lung carcinomas or B16FIO melanomas were grown in the dorsal subcutaneous space of adult female ephrinB2$^{taulacZ/+}$ mice as previously described (O'Reilly, M. S., et al., *Cell* 88(2):277–285 (1997)). Tumors were measured in two dimensions by calipers on a daily basis and volume was calculated as width$^2$×length×0.52. Mice bearing 200 mm$^3$ tumors were anesthetized, sacrificed and tumors were embedded in OCT and sectioned at 20 μm. Slides were air-dried and fixed in 2% PFA/0.1 M PIPES buffer (pH 7.0). Sections were stained in X-Gal buffer at 30° C. for 3 hours, post-fixed with 2% PFA/PBS and processed for immunostaining using anti-PECAM-1 antibody (clone MEC 13.3, 0.5 μg/ml), a biotinylated secondary antibody (1:200; Jackson Immuno Research Laboratories, Bar Harbor, Me.) followed by ABC peroxidase complexes and AEC/H$_2$O$_2$ chromagen-substrate.

Results

We used ephrinB2$^{taulacZ/+}$ indicator mice to determine whether ephrinB2 is expressed in different settings of adult neovascularization. One model system is the corneal micropocket assay (Kenyon et al., *Invest. Opthamol Vis. Sci.* 37:1625–1632 (1996)). Implantation of a pellet of VEGF into a corneal micropocket caused new ephrinB2$^+$ vessels to sprout from the limbus artery towards the pellet (see, e.g, U.S. Provisional Application No. 60/252,009, filed on Nov. 20, 2000, FIG. 6A–6C). Double-labeling using X-Gal and anti-PECAM-1 immunoperoxidase histochemistry indicated that ephrinB2 expression was detected in a subset of the ingrowing vessels, and extended into the smallest-diameter capillaries of the microvasculature (see, e.g, U.S. Provisional Application No. 60/252,009, filed on Nov. 20, 2000, FIG. 6D and 6E). This was confirmed by double-label immunofluorescence staining with antibodies to β-galactosidase and PECAM-1 (see, e.g, U.S. Provisional Application No. 60/252,009, filed on Nov. 20, 2000, FIG. 6H, arrowheads). To verify that expression of ephrinB2 occurred in newly formed rather than pre-existing vessels, dividing endothelial cells were labeled in vivo by an injection of BrdU and the tissue processed for double-label immunofluorescence staining with antibodies to BrdU and β-galactosidase. This experiment confirmed that ephrinB2$^+$ vessels growing into the cornea indeed contained BrdU$^+$ cells (see, e.g, U.S. Provisional Application No. 60/252,009, filed on Nov. 20, 2000, FIG. 6K, arrowheads) and therefore represented neovascularization.

We also examined ephrinB2 expression in a more physiological setting of neovascularization, namely wound-healing. Strong staining in what appeared to be blood vessels was apparent in wounded tissue undergoing healing (see, e.g, U.S. Provisional Application No. 60/252,009, filed on Nov. 20, 2000, FIG. 7A and 7B). This was confirmed by double-labeling with X-Gal histochemistry and anti-PECAM-1 antibody staining (see, e.g, U.S. Provisional Application No. 60/252,009, filed on Nov. 20, 2000, FIG. 7C and 7D), which also indicated that ephrinB2 was expressed by a subset of the small vessels in the wounded region (see, e.g, U.S. Provisional Application No. 60/252,009, filed on Nov. 20, 2000, FIG. 7C and 7D). Staining was also detected in a subset of vessels in normal skin, albeit at apparently lower levels.

We further addressed the question of whether ephrinB2 is expressed during tumor angiogenesis by implanting either Lewis Lung carcinoma or B16 Melanoma cells subcutaneously into EphrinB2$^{taulacZ/+}$ indicator mice. After several weeks, the tumors were sectioned and double-labeled by X-Gal immunohistochemistry and anti-PECAM-1 antibody staining. In both cases, extensive expression of ephrinB2 was observed within the tumor vasculature (see, e.g, U.S. Provisional Application No. 60/252,009, filed on Nov. 20, 2000, FIG. 8A and 8B). Double labeling confirmed that the ephrinB2$^+$ elements were indeed PECAM-1$^+$ blood vessels (see, e.g, U.S. Provisional Application No. 60/252,009, filed on Nov. 20, 2000, FIG. 8C and 8D, arrows), and indicated that a subset of the PECAM-1$^+$ vessels were ephrinB2$^-$ in both tumor models (see, e.g, U.S. Provisional Application No. 60/252,009, filed on Nov. 20, 2000, FIG. 8B–8D).

Thus, these studies clearly indicate that ephrinB2 is expressed in subsets of microvessels in several settings of adult neovascularization, including wound healing and tumor angiogenesis. The studies also indicate that in addition to embryonic angiogenesis, ephrinB2, EphB4 and the signaling that occurs between them functions in neovascularization.

Discussion (Expression of EphrinB2 in Adult Neovascularization)

Using adult indicator mice, we have obtained evidence that ephrinB2 is expressed at sites of adult neovascularization in three different settings: VEGF-induced angiogenesis in the cornea, cutaneous wound healing and tumor angiogenesis. In each case, the marker is expressed in a subset of newly forming vessels, strongly suggesting that such vessels have arterial or venous identity that may be important for the formation of the new vascular circuitry. These observations challenge prevailing concepts about the topology of neovascularization. For example, in both corneal neovascularization and tumor angiogenesis, it has been thought that pairs of new vessels sprout from the post-capillary venule to form a "bucket-handle"-like structure that shunts blood out of the venule into the neighboring tissue (Gimbrone, M. A., Jr., et al., *J. Natl Cancer Inst.* 52:413–427 (1974); Grunt, T. W., et al., *Scan. Electron Microsc.* 2:557–573 (1986)). How such loops, acquire an afferent and efferent sidedness has not been explained, however. Our data in the cornea clearly reveal ephrinB$^{2+}$ vessels sprouting towards the VEGF pellet implant (see, e.g, U.S. Provisional Application No. 60/252, 009, filed on Nov. 20, 2000, FIG. 6). The presence of this arterial marker suggests that the traditional classification of all sprouts as being of venous origin, based purely on morphological criteria, may have been incorrect. If a subset of neovessels sprout from arteries and connect with corresponding sprouts deriving from veins, it could explain how the 'bucket-handle' structure develops with an intrinsic afferent-efferent polarity. A similar scenario could occur during tumor angiogenesis. More detailed studies of the topological origin of ephrinB2$^+$ vessels in tumor angiogenesis and their relationship to neovessels derived from the post-capillary venules should shed further light on this issue.

The fact that ephrinB2 is expressed at sites of neovascularization, taken together with its essential requirement for angiogenesis in the embryo, suggests that this ligand (and by extension, its receptor(s) (Gerety, S. S., et al., *Mol. Cell* 4:403–414 (1999))) may be functionally important for adult blood vessel remodeling as well. In support of this idea, other ligand-receptor systems initially shown to be important in embryonic angiogenesis have also proven essential for adult neovascularization (reviewed in (Yancopoulos, G. D., et al., *Cell* 93:661–664 (1998))). It is currently not yet possible to examine this in ephrinB2 knockout mice because of the embryonic lethality of the homozygous mutation. However, conditional knockouts of the gene in the adult vasculature should provide one approach to addressing this question. If ephrinB2 and its receptor(s) prove to be important in adult neovascularization, it would suggest that pharmacologic manipulation of this ligand-receptor interaction may provide an alternative route to pro- and anti-angiogenic therapies for heart disease and cancer, respectively (Folkman, J., *Circulation* 97:628–629 (1998); Folkman, J., *Proc. Natl. Acad. Sci. USA* 95:9064–9066 (1998)), as has been demonstrated for other signaling systems important in angiogenesis (Lin, P., et al., *Proc. Natl. Acad. Sci. USA* 95:8829–8834 (1998)).

Significance of Examples 14–16

EphrinB2 and its receptor EphB4 are expressed by developing arteries and veins, respectively, and are essential for embryonic heart development and angiogenesis (Adams, R., et al., *Genes Dev.* 13:295–306 (1999); Gerety, S. S., et al., *Mol. Cell* 4:403–414 (1999); Wang, H. U., et al., *Cell* 93:741–753 (1998)). As described herein, the specific expression of this ligand-receptor pair in arterial and venous endothelial cells, respectively, persists into adulthood in most tissues we examined. Moreover, ephrinB2 is also expressed in arterial smooth muscle cells, however, the initiation of this expression in development is delayed by several days in relation to its onset in the endothelium. In addition to its steady-state expression in mature vessels, ephrinB2 expression is also observed in newly forming blood vessels in several settings of adult angiogenesis.

These findings are significant for several reasons. First, they indicate that molecular distinctions between arteries and veins are not simply a transient feature of the developing circulatory system, but persist into adulthood as well. Second, they identify a stable genetic difference between the smooth muscle cells of arteries and veins. Third, they challenge several traditional concepts about the identity of vessels in capillary beds and during neovascularization. Finally, because the particular molecules that serve as markers of vessel identity in this case are functionally essential for embryonic angiogenesis, they may play an important role in the maintenance and/or remodeling of the adult circulatory system.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for assessing an effect of an agent on arterial smooth muscle cells, comprising
   a) adding said agent to arterial smooth muscle cells expressing Ephrin B2; and
   b) comparing the effect of said agent on said arterial smooth muscle cells with a suitable control,
   wherein comparing the effect comprises:
   (i) measuring Ephrin B2 gene expression;
   (ii) detecting Ephrin B2 binding to an EphB4 receptor; or
   (iii) measuring Ephrin B2 activation or inhibition.

2. The method of claim 1, wherein the suitable control comprises arterial smooth muscle cells in the absence of said agent.

3. The method of claim 1, wherein the agent is selected from the group consisting of an antibody and an antigen-binding fragment thereof.

4. The method of claim 1, wherein the agent is selected from the group consisting of a peptide, a polypeptide, a peptoid, a sugar, a hormone, and a nucleic acid molecule.

5. The method of claim 4, wherein the agent is a polypeptide comprising an extracellular domain of EphB4.

6. The method of claim 1, wherein the agent comprises a label selected from the group consisting of a fluorescent label, a colorimetric label, an enzyme label, an affinity label, an epitope label, a spin label, and a chemiluminescent group.

7. The method of claim 1, wherein the arterial smooth muscle cells are cells of an arterial smooth muscle cell line.

8. The method of claim 1, wherein Ephrin B2 gene expression is measured by monitoring expression of an indicator gene that is inserted in the Ephrin B2 gene.

* * * * *

SEQUENCE LISTING

<160> NUMBER OF SEQ ID NOS: 4

<210> SEQ ID NO 1

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
aagatggatt gcacgcaggt tctc                                            24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
cctgatgctc ttcgtccaga tcat                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
aggacggagg acgttgccac taac                                            24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
accaccagtt ccgacgcgaa ggga                                            24
```